United States Patent
Hu et al.

(10) Patent No.: US 11,976,129 B2
(45) Date of Patent: May 7, 2024

(54) MONOCLONAL ANTIBODY SPECIFICALLY BINDING HUMAN AND MONKEY CD38 ANTIGENS, PREPARATION METHOD AND USE THEREOF

(71) Applicant: Acroimmune Biotech Co., Ltd., Guangzhou (CN)

(72) Inventors: Hongqun Hu, Suzhou (CN); Xiaoqi Song, Suzhou (CN); Zui Chen, Suzhou (CN); Xiaoxiao Ma, Suzhou (CN); Yanping Yuan, Suzhou (CN); Qunmin Zhou, Suzhou (CN)

(73) Assignee: ACROIMMUNE BIOTECH CO., LTD., Guangzhou (CN)

( * ) Notice: Subject to any disclaimer, the term of this patent is extended or adjusted under 35 U.S.C. 154(b) by 695 days.

(21) Appl. No.: 17/274,439

(22) PCT Filed: Sep. 27, 2018

(86) PCT No.: PCT/CN2018/107812
§ 371 (c)(1),
(2) Date: Mar. 9, 2021

(87) PCT Pub. No.: WO2020/056790
PCT Pub. Date: Mar. 26, 2020

(65) Prior Publication Data
US 2021/0324102 A1 Oct. 21, 2021

(30) Foreign Application Priority Data
Sep. 19, 2018 (CN) .......................... 201811090932.4

(51) Int. Cl.
| | | |
|---|---|---|
| C07K 16/18 | (2006.01) | |
| A61K 45/06 | (2006.01) | |
| A61P 35/00 | (2006.01) | |
| C07K 1/22 | (2006.01) | |
| C07K 16/28 | (2006.01) | |
| A61K 39/00 | (2006.01) | |

(52) U.S. Cl.
CPC .......... *C07K 16/2896* (2013.01); *A61K 45/06* (2013.01); *A61P 35/00* (2018.01); *C07K 1/22* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 7,829,673 B2 | 11/2010 | De Weers et al. | |
| 9,580,498 B2 | 2/2017 | Luo et al. | |
| 11,105,818 B2 * | 8/2021 | Su et al. | ................. G01N 33/74 |

FOREIGN PATENT DOCUMENTS

| | | | | |
|---|---|---|---|---|
| AU | 2004299833 A1 | 6/2005 | | |
| CN | 103865878 A | 6/2014 | | |
| CN | 107033243 A | 8/2017 | | |
| CN | 107365385 A | 11/2017 | | |
| CN | 108350077 A | 7/2018 | | |
| JP | 2016034954 A | 3/2016 | | |
| JP | WO 2017/179718 A1 * | 10/2017 | ......... | G01N 33/5044 |
| WO | 2006099875 A1 | 9/2006 | | |
| WO | 2018192089 A1 | 10/2018 | | |

OTHER PUBLICATIONS

David G. Jackson, et al., Isolation of a cDNA Encoding the Human Cd38 (T10) Molecule, A Cell Surface Glycoprotein with an Unusual Discontinuous Pattern of Expression During Lymphocyte Differentiation, The Journal of Immunology, 1990, pp. 2811-2815, vol. 144 No. 7.
Nobuyuki Harada, et al., Expression Cloning of a cDNA Encoding a Novel Murine B Cell Activation Marker, The Journal of Immunology, 1993, pp. 3111-3118, vol. 151 No. 6.
Enza Ferrero, et al., Characterization and phylogenetic epitope mapping of CD38 ADPR cyclase in the cynomolgus macaque, BMC Immunology, 2004, pp. 1-13, 5:21.
David J. States, et al., Similarities in amino acid of sequences of Aplysia ADP-ribosyl cyclase and human lymphocyte antigen CD38, Trends Biochem. Sci., 1992, pp. 495, vol. 17.
Maureen Howard, et al., Formation and Hydrolysis of Cyclic ADP-Ribose Catalyzed by Lymphocyte Antigen CD38, Science. 1993, pp. 1056-1059, vol. 262 No. 105.
Robin J. Summerhill, et al., Human lymphocyte antigen CD38 catalyzes the production of cyclic ADP-ribose, FEBS Lett., 1993, pp. 231-233, vol. 335 No. 2.
G. Sridhar Prasad, et al. Crystal structure of Aplysia ADP ribosyl cyclase, a homologue of the bifunctional ectezyme CD38, Nature Structural Biology, 1996, pp. 957-964, vol. 3 No. 11.
Kapil Mehta, et al., Human CD38, a cell-surface protein with multiple functions, FASEB J., 1996, pp. 1408-1417, 10.
George Shubinsky, et al., The CD38 Lymphocyte Differentiation Marker: New Insight into Its Ectoenzymatic Activity and Its Role as a Signal Transducer, Immunity, 1997, pp. 315-324, vol. 7.

(Continued)

*Primary Examiner* — Kevin S Orwig
*Assistant Examiner* — Estella M. Gustilo
(74) *Attorney, Agent, or Firm* — Bayramoglu Law Offices LLC

(57) ABSTRACT

A monoclonal antibody specifically binding to human and monkey CD38 antigens or a derivative thereof includes: antigen complementarity-determining regions CDR1, CDR2 and CDR3 of an antibody light chain variable region having amino acid sequences as set forth in SEQ ID NO: 3, SEQ ID NO: 4 and SEQ ID NO: 5, respectively; and antigen complementarity-determining regions CDR1, CDR2 and CDR3 of an antibody heavy chain variable region having amino acid sequences as set forth in SEQ ID NO: 8, SEQ ID NO: 9 and SEQ ID NO: 10, respectively. The monoclonal antibody or derivative thereof can be used as a component of a pharmaceutical composition or prepared into a suitable pharmaceutical preparation, administered alone or combined with other therapeutic means such as chemotherapy drugs, for treating tumors with positive CD38 expression, such as human myeloma and human lymphoma.

19 Claims, 23 Drawing Sheets

Specification includes a Sequence Listing.

(56) References Cited

OTHER PUBLICATIONS

Ellis L. Reinherz, et al. Discrete stages of human intrathymic differentiation: Analysis of normal thymocytes and leukemic lymphoblasts of T-cell lineage, Proc. Natl. Acad. Sci., 1980, pp. 1588-1592, vol. 77 No. 3.

Freda K. Stevenson, et al. Preliminary Studies for an Immunotherapeutic Approach to the Treatment of Human Myeloma Using Chimeric Anti-CD38 Antibody, Blood, 1991, pp. 1071-1079, vol. 77 No. 5.

Victor S. Goldmacher, et al., Anti-CD38-Blocked Ricin: An Immunotoxin for the Treatment of Multiple Myeloma, Blood, 1994, pp. 3017-3025, vol. 84 No. 9.

Jonathan H. Ellis, et al., Engineered Anti-CD38 Monoclonal Antibodies for Immunotherapy of Multiple Myeloma, J Immunol., 1995, pp. 925-937, vol. 155.

Michel De Weers, et al., Daratumumab, a Novel Therapeutic Human CD38 Monoclonal Antibody, Induces Killing of Multiple Myeloma and Other Hematological Tumors, The Journal of Immunology, 2011, pp. 1840-1848, vol. 186.

H.M. Lokhorst, et al., Targeting CD38 with Daratumumab Monotherapy in Multiple Myeloma, The New England Journal of Medicine, 2015, pp. 1207-1219, vol. 373 No. 13.

Sagar Lonial, et al., Daratumumab monotherapy in patients with treatment-refractory multiple myeloma (SIRIUS): an open-label, randomised, phase 2 trial, Lancet, 2016, pp. 1551-1560, 387.

M.A. Dimopoulos, et al., Daratumumab, Lenalidomide, and Dexamethasone for Multiple Myeloma, The New England Journal of Medicine, 2016, vol. 1319-31, vol. 375 No. 14.

Antonio Palumbo, et al.,Daratumumab, Bortezomib, and Dexamethasone for Multiple Myeloma, The New England Journal of Medicine, 2016, pp. 754-766, vol. 375 No. 8.

Ajai Chari, et al. Daratumumab plus pomalidomide and dexamethasone in relapsed and/or refractory multiple myeloma, Clinical Trials and Observations, Blood. 2017, pp. 974-981, vol. 130 No. 8.

M.-V. Mateos, et al., Daratumumab plus Bortezomib, Melphalan, and Prednisone for Untreated Myeloma,The New England Journal of Medicine, 2018, pp. 518-528, vol. 378 No. 6.

Eva Klein, et al, Surface IgM-kappa Specificity on a Burkitt Lymphoma Cell In Vivo and in Derived Culture Lines, Cancer Research, 1968, pp. 1300-1310, vol. 28.

R. J. V. Pulvertaft, Cytology of Burkitt's Tumour (African Lymphoma), The Lancet, 1964, pp. 238-240.

Y. Matsuoka, et al., Production of Free Light Chains of Immunoglobulin by a Hematopoietic Cell Line Derived from a Patient with Multiple Myeloma, Experimental Biology and Medicine, 1967, pp. 1246-1250, vol. 125.

J. Minowada, et al. Brief Communication: Rosette-Forming Human Lymphoid Cell Lines. I. Establishment and Evidence for Origin of Thymus-Derived Lymphocytes, Journal of the National Cancer Institute, 1972, pp. 891-895, vol. 49.

Steven Gillis, et al., Biochemical and Biological Characterization of Lymphocyte Regulatory Molecules, J. Exp. Med., 1980, pp. 1709-1719, vol. 152.

Inger S. Nijhof, et al., Preclinical Evidence for the Therapeutic Potential of CD38-Targeted Immuno-Chemotherapy in Multiple Myeloma Patients Refractory to Lenalidomide and Bortezomib, Clinical Cancer Research, 2015, pp. 2802-2810, vol. 21 No. 12.

Torben Plesner, et al., Phase 1/2 study of daratumumab, lenalidomide, and dexamethasone for relapsed multiple myeloma, Clinical Trials and Observations, Blood, 2016, pp. 1821-1828, vol. 128 No. 14.

Niels W. C. J. Van De Donk, et al., Monoclonal antibodies targeting CD38 in hematological malignancies and beyond, Immunological Reviews, 2016, pp. 95-112, vol. 270.

Ting Wu, et al., Research Progresses of Daratumumab Targeted Treatment for Multiple Myeloma, Life Science Research, 2017, pp. 349-354, vol. 21 No. 4.

Huan Wang, et al., Advances in the Diagnosis and Therapy of Primary Plasma Cell Leukemia, Journal of Experimental Hematology, 2017, pp. 1837-1841, vol. 25 No. 6.

Ying Wang., et al, Degenerated primer design to amplify the heavy chain variable region from immunoglobulin cDNA, BMC Bioinformatics, 2006, pp. 1-7, 7(Suppl 4): S9.

G. Köhler, et al., Continuous cultures of fused cells secreting antibody of predefined specificity, Nature, 1975, pp. 495-497, vol. 256.

Elvin A. Kabat, et al., Sequences of Proteins of Immunological Interest, National Institutes of Health, 1991, pp. 647-669, vol. 1, Publ. No. 91-3242.

* cited by examiner

Identities: 177/300(59%)   Positive:220/300(73%)

```
hCD38   1    MANCEFSPVSGDKPCCRLSRR AQLCLGVSILVLILVVVLAVVV---  PRWRQQWSGPGTTK   57
             MAN EFS VSGD+P CRLSR+AQ+ LGV +LVLI +VV VV+    PR   W+G  TTK
mCD38   1    MANYEFSQVSGDRPGCRLSRK AQIGLGVGLLVLIALVVGIVVILE RPRSLLVWTGEPTTK   60 hCD38  58    RFPETVLARCVKYTEI-HPEMRHVDCQSVWDAFKGAFISKHPCNITEEDYQPLMKLGTQT   116
             F + L RC+ YT+I  PEMR +CQ +    FKGAF+SK+PCNIT EDY PL+KL TQT
mCD38  61    RFSDIFLGRCLIYTQILRPEMRDQNCQEILSTFKGAFVSKNPCNITREDYAPLVKLVTQT   120 hCD38 117    VPCNKILLWSRIKDLAHQFTQVQRDMFTLEDTLLGYLADDLTWCGEFNTSKINYQSCPDW   176
             +PCNK L WS+ K LAHQ+T +Q MFTLEDTLLGY+ADDL WCG+ +TS +NY SCP W
mCD38 121    IPCNKTLFWSKSKHLAHQYTWIQGKMFTLEDTLLGYIADDLRWCGDPSTSDMNYVSCPHW   180 hCD38 177    RKDCSNNPVSVFWKTVSRRFAEAACDVVHVMLNGSRSKIFDKNSTFGSVEVHNLQPEKVQ   236
             ++C NNP++VFWK +S++FAE AC VV VMLNGS + F KNSTFGSVEV +L P KV
mCD38 181    SENCPNNPITVFWKVISQKFAEDACGVVQVMLNGSLREPFYKNSTFGSVEVFSLDPNKVH   240 hCD38 237    TLEAWVIHGGREDSRDLCQDPTIKELESIISKRNIQFSCKNIYRPDKFLQCVKNPEDSSC   296
             L+AWV+H    S + C  ++ EL+ I+  KRN+F+C + YRP +FLQCVKNPE SC
mCD38 241    KLQAWVMHDIEGASSNACSSSSLNELKMIVQKRNMIFACVDNYRPARFLQCVKNPEHPSC   300
```

FIG. 1

A. CDC on Daudi cells

A. Identities: 66/112(59%)

```
m39L   1   XIVXTQXPXXLXXXXGXXAXISC RSQSXXXXXXXTYLX WYXQKPGQXPXLLIY XXSNXXX  61
           IV+TQ+P +L + G++A++SCR+SQS+      ++YL WY QKPGQ+P+LLIY   SNR
DaraL  1   EIVLTQSPATLSLSPGERATLSC RASQSV------SSYLA WYQQKPGQAPRLLIY DASNRAT  66 m39L  62   GXPXRFSGSGSGTDFTLXISXXEXEDXXVYC XQXSXXPXTF GXGTKXEIK  112
           G+P RFSGSGSGTDFTL IS +E ED  VY+C Q S+ P TFG GTK+EIK
DaraL 57   GIPARFSGSGSGTDFTLTISSLEPEDFAVYYC QQRSNWPPTF GQGTKVEIK  107
```

FIG. 7A

B. Identities: 50/123(41%)

```
39H    1   XVQLXXSXXXLXXPGXSXXLSCXXXX XXXFXTSY MSWVRQXPGXGXEWXX XIXXXXGXXX  60
           +VQL +S   L  PG S++LSC        F +  MSWVRQ PG G EW+   I  + G  +
DaraH  1   EVQLLESGGGLVQPGGSLRLSCA-VS GFTFNSFA MSWVRQAPGKGLEWVS AISGSGGGTY  59

39H   61   YXXXXX XXXXXXXDXXXNTXYLXXXSLXXEDXAXYXCAX XX---XG-XXXXY WGQGTLVXVSX  119
            Y +  +   +   D   NT YL++ SL +ED+A+Y+CA++    +G +    YWGQGTLV VS+
DaraH 60   YADSVK GRFTISRDNSKNTLYLQMNSLRAEDTAVYFCAK DKILWFGEPVFDY WGQGTLVTVSS  122
```

FIG. 7B

A. CHO-human CD38 (wild-type)

B. CHO-human CD38 ($S_{274F}$ mutation)

Identities between human CD38 (huCD38) and monkey CD38 (MkCD38): 275/301 (91%)

Chimpanzee CD38 (ChCD38) and human CD38 (huCD38) only three different amino acids

```
ChCD38   1  MANCEFSPVSGDKPCCRLSRRAQLCLGVSILVLILVVVLAVVV PRWRQQWSGPGTTKRFP60
huCD38   1  MANCEFSPVSGDKPCCRLSRRAQLCLGVSILVLILVVVLAVVV PRWRQQWSGPGTTKRFP60
MkCD38   1  MANCEFSPVSGDKPCCRLSRRAQVCLGVCLLVLLILVVVVAVVIPRWRQQWSGSGTTSRFP61

ChCD38  61  ETVLARCVKYTEIHPEMRHVDCQSVWDAFKGAFISKHPCNITEEDYQPLMKLGTQTVPCN120
huCD38  61  ETVLARCVKYTEIHPEMRHVDCQSVWDAFKGAFISKHPCNITEEDYQPLMKLGTQTVPCN120
MkCD38  62  ETVLARCVKYTEVHPEMRHVDCQSVWDAFKGAFISKYPCNITEEDYQPLVKLGTQTVPCN121

ChCD38 121  KILLWSRIKDLAHQFTQVQRDMFTLEDTLLGYLADDLTWCGEFNTSKINYQSCPDWRKDC180
huCD38 121  KILLWSRIKDLAHQFTQVQQDMFTLEDTLLGYLADDLTWCGEFSTSEINYQSCPDWRKDC180
MkCD38 122  KTLLWSRIKDLAHQFTQVQRDMFTLEDMLLGYLADDLTWCGEFNTFEINYQSCPDWRKDC181

ChCD38 181  SNNPVSVFWKTVSRRFAEAACDVVHVMLNGSRSKIFDKNSTFGSVEVHNLQPEKVQTLEA240
huCD38 181  SNNPVSVFWKTVSRRFAEAACDVVHVMLNGSRSKIFDKNSTFGSVEVHNLQPEKVQTLEA240
MkCD38 182  SNNPVSVFWKTVSRRFAETACGVVHVMLNGSRSKIFDKNSTFGSVEVHNLQPEKVQALEA241

ChCD38 241  WVIHGGREDSRDLCQDPTIKELESIISKRNIQFSCKNIYRPDKFLQCVKNPEDSSCTSEI300
huCD38 241  WVIHGGREDSRDLCQDPTIKELESIISKRNIQFSCKNIYRPDKFLQCVKNPEDSSCTSEI300
MkCD38 242  WVIHGGREDSRDLCQDPTIKELESIISKRNIPFFCKNIYRPDKFLQCVKNPEDSSCLSGI301
```

FIG. 11A

SEQUENCE LISTING

<160> NUMBER OF SEQ ID NOS: 23

<210> SEQ ID NO 1
<211> LENGTH: 336
<212> TYPE: DNA
<213> ORGANISM: Mus musculus

<400> SEQUENCE: 1

```
gacattgtga tgacccaaac tccactctcc cttcctgtcg gtcttggaga tcaagcctcc      60
atctcttgca gatctagtca gagccttcta cacagtaatg gaaacaccta tttacattgg     120
tacctgcaga agccaggcca gtctccaaag ctcctgatct acaaagtttc caaccgattt     180
tctggggtcc cagacagatt cagtggcagt ggatcaggga cagatttcac actcaagatc     240
agtagagtgg aggctgagga tctgggagtt tatttctgct ctcaaagttc acatcttccg     300
tggacgttcg gtggaggcac caagctggaa atcaaa                                336
```

<210> SEQ ID NO 2
<211> LENGTH: 112
<212> TYPE: PRT
<213> ORGANISM: Mus musculus

<400> SEQUENCE: 2

```
Asp Ile Val Met Thr Gln Thr Pro Leu Ser Leu Pro Val Gly Leu Gly
1               5                   10                  15
Asp Gln Ala Ser Ile Ser Cys Arg Ser Ser Gln Ser Leu Leu His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Ser His Leu Pro Trp Thr Phe Gly Gly Gly Thr Lys Leu Glu Ile Lys
            100                 105                 110
```

<210> SEQ ID NO 3
<211> LENGTH: 16
<212> TYPE: PRT
<213> ORGANISM: Mus musculus

<400> SEQUENCE: 3

```
Arg Ser Ser Gln Ser Leu Leu His Ser Asn Gly Asn Thr Tyr Leu His
1               5                   10                  15
```

<210> SEQ ID NO 4
<211> LENGTH: 7
<212> TYPE: PRT
<213> ORGANISM: Mus musculus

<400> SEQUENCE: 4

```
Lys Val Ser Asn Arg Phe Ser
1               5
```

<210> SEQ ID NO 5
<211> LENGTH: 10
<212> TYPE: PRT
<213> ORGANISM: Mus musculus

<400> SEQUENCE: 5

```
Ser Gln Ser Ser His Leu Pro Trp Thr Phe
1               5                   10
```

<210> SEQ ID NO 6
<211> LENGTH: 357
<212> TYPE: DNA
<213> ORGANISM: Mus musculus

<400> SEQUENCE: 6

```
caggttcagc tgcagcagtc tgtttctgaa ctgaggagtc ctgggtcttc agtaaagctt    60
tcatgcaagg attttgattc agaggttttc cctacttctt atatgagttg ggttaggcag   120
aagcctgggc atggatttga gtggattgga gacatactcc caaatattgg tagaatattc   180
tatggagaga aatttgagga caaagccaaa ctggatgcag acacagtgtc caacacagcc   240
tacttggagc tcaccagcct gtcatctgag gactctgcta tctactattg tgcaagggag   300
gcctacggca gtatccttgg ttactggggc caagggactc tggtcgctgt ctctgca      357
```

<210> SEQ ID NO 7
<211> LENGTH: 119
<212> TYPE: PRT
<213> ORGANISM: Mus musculus

<400> SEQUENCE: 7

```
Gln Val Gln Leu Gln Gln Ser Val Ser Glu Leu Arg Ser Pro Gly Ser
1               5                   10                  15

Ser Val Lys Leu Ser Cys Lys Asp Phe Asp Ser Glu Val Phe Pro Thr
            20                  25                  30

Ser Tyr Met Ser Trp Val Arg Gln Lys Pro Gly His Gly Phe Glu Trp
        35                  40                  45

Ile Gly Asp Ile Leu Pro Asn Ile Gly Arg Ile Phe Tyr Gly Glu Lys
    50                  55                  60

Phe Glu Asp Lys Ala Lys Leu Asp Ala Asp Thr Val Ser Asn Thr Ala
65                  70                  75                  80

Tyr Leu Glu Leu Thr Ser Leu Ser Ser Glu Asp Ser Ala Ile Tyr Tyr
                85                  90                  95

Cys Ala Arg Glu Ala Tyr Gly Ser Ile Leu Gly Tyr Trp Gly Gln Gly
            100                 105                 110

Thr Leu Val Ala Val Ser Ala
        115
```

```
<210> SEQ ID NO 8
<211> LENGTH: 8
<212> TYPE: PRT
<213> ORGANISM: Mus musculus

<400> SEQUENCE: 8

Ser Glu Val Phe Pro Thr Ser Tyr
1               5

<210> SEQ ID NO 9
<211> LENGTH: 16
<212> TYPE: PRT
<213> ORGANISM: Mus musculus

<400> SEQUENCE: 9

Asp Ile Leu Pro Asn Ile Gly Arg Ile Phe Tyr Gly Glu Lys Phe Glu
1               5                   10                  15

<210> SEQ ID NO 10
<211> LENGTH: 9
<212> TYPE: PRT
<213> ORGANISM: Mus musculus

<400> SEQUENCE: 10

Glu Ala Tyr Gly Ser Ile Leu Gly Tyr
1               5

<210> SEQ ID NO 11
<211> LENGTH: 112
<212> TYPE: PRT
<213> ORGANISM: Artificial Sequence
<220> FEATURE:
<223> OTHER INFORMATION: Sequence is synthesized

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ser His Leu Pro Trp Thr Phe Gly Gly Gly Thr Lys Leu Glu Ile Lys
            100                 105                 110

<210> SEQ ID NO 12
<211> LENGTH: 118
<212> TYPE: PRT
<213> ORGANISM: Artificial Sequence
<220> FEATURE:
<223> OTHER INFORMATION: Sequence is synthesized

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Ser Glu Val Phe Pro Thr Ser
            20                  25                  30
```

```
Tyr Met Ser Trp Val Arg Gln Ala Pro Gly Gln Gly Leu Glu Trp Met
        35                  40                  45
Gly Asp Ile Leu Pro Asn Ile Gly Arg Ile Phe Tyr Gly Glu Lys Phe
 50                  55                  60
Glu Asp Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Ala Tyr Gly Ser Ile Leu Gly Tyr Trp Gly Gln Gly Thr
            100                 105                 110
Leu Val Ala Val Ser Ala
        115

<210> SEQ ID NO 13
<211> LENGTH: 336
<212> TYPE: DNA
<213> ORGANISM: Artificial Sequence
<220> FEATURE:
<223> OTHER INFORMATION: Sequence is synthesized

<400> SEQUENCE: 13
gacatcgtga tgacccagac ccctctgtct ttaagcgtga cccccggtca gcccgcttcc      60
atcagctgtc gtagctccca gtctttactg cactccaacg gcaacaccta tttacactgg    120
tatttacaga agcccggcca gtcccctcag ctgctgatct acaaggtgtc caaccggttc    180
tccggcgtgc ccgatcgttt ttccggttct ggctccggca ccgacttcac tttaaaaatt    240
tctcgtgtgg aggccgagga cgtgggcgtg tactactgct cccagtcctc ccatttacct    300
tggacctttg gcggcggcac caagctggag atcaag                               336

<210> SEQ ID NO 14
<211> LENGTH: 354
<212> TYPE: DNA
<213> ORGANISM: Artificial Sequence
<220> FEATURE:
<223> OTHER INFORMATION: Sequence is synthesized

<400> SEQUENCE: 14
caagttcagc tggtgcagtc cggcgctgag gtgaagaagc ccggctccag cgtgaaggtg      60
tcttgtaagg cctcctccga ggtgttcccc acctcctaca tgtcttgggt gaggcaagct    120
cccggtcaag gtttagagtg gatgggcgac attttaccca acatcggtcg tatcttctac    180
ggcgagaagt tcgaggatcg tgtgaccatc accgccgaca gtccacctc caccgcctac    240 atggagctgt cctctttaag gtccgaggac accgccgtgt actactgcgc tcgtgaggct    300
tacggctcca ttttaggcta ttggggccaa ggtacactgg tggccgtgtc cgcc          354

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
ttgtaagctt gccgccacca tggctaactg cgagttctcc                            40

<210> SEQ ID NO 16
<211> LENGTH: 59
<212> TYPE: DNA
<213> ORGANISM: Artificial Sequence
```

-continued

```
<220> FEATURE:
<223> OTHER INFORMATION: primer

<400> SEQUENCE: 16
cttatcgggc ctatagatat ttttgcagaa gaactggatg ttccgcttgc tgatgatgc      59

<210> SEQ ID NO 17
<211> LENGTH: 85
<212> TYPE: DNA
<213> ORGANISM: Artificial Sequence
<220> FEATURE:
<223> OTHER INFORMATION: primer

<400> SEQUENCE: 17
tggtctcgag tcagatctcg gaggtgcagc tggagtcttc ggggttcttc acgcactgta     60
aaaacttatc gggcctatag atatt                                          85

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tgtcgttcac tgccatcaat                                                 20

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gcaaggctta caaccacaat c                                               21

<210> SEQ ID NO 20
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(17)
<223> OTHER INFORMATION: w is A or T;   m is A or C

<400> SEQUENCE: 20
gacattgtga tgwcmca                                                    17

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ctgaggcacc tccagatgtt                                                 20

<210> SEQ ID NO 22
<211> LENGTH: 15
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (1)..(15)
<223> OTHER INFORMATION: r is A or G;    y is C or T

<400> SEQUENCE: 22
carctgcarc aryct                                                        15

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gtgctggagg ggacagtcac t                                                 21
```

MONOCLONAL ANTIBODY SPECIFICALLY BINDING HUMAN AND MONKEY CD38 ANTIGENS, PREPARATION METHOD AND USE THEREOF

CROSS REFERENCE TO THE RELATED APPLICATIONS

This application is the national phase entry of International Application No. PCT/CN2018/107812, filed on Sep. 27, 2018, which is based upon and claims priority to Chinese Patent Application No. 201811090932.4, filed on Sep. 19, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHHY014_Sequence Listing.txt, created on Mar. 1, 2021 and is 9,769 bytes in size.

TECHNICAL FIELD

The present invention belongs to the field of biotechnology involving monoclonal antibodies. The present invention relates to a monoclonal antibody, specifically binding human and monkey CD38 antigen, as well as preparation method and use thereof.

BACKGROUND

CD38 (also known as T10, an antigen recognized by OKT10 monoclonal antibody) is a 45KD type H transmembrane glycoprotein. cDNA coding human and mouse CD38 gene was cloned and reported in the early 1990s (Jackson D G and Bell J I. J. Immunol. 1990, 144:2811-2815; Harada et al. J Immunol. 1993, 151:3111-8); cDNA coding cynomolgus macaque CD38 gene was cloned and reported in 2004 (Ferrero E et al, BMC Immunol. 2004, 5:21). There are 300 amino acids in full length in human CD38 protein. Among them, 21 amino acids at N-terminal are located inside the cell, 22 amino acids are located in the cell membrane, and 257 amino acids at C-terminal are located outside the cell membrane. There are 301 amino acids in full length in cynomolgus macaque CD38 protein, and the identity with the amino acid sequence of human CD38 protein is 92%; while there are 304 amino acids in full length in mouse CD38 protein, and the identity with the amino acid sequence of human CD38 protein is about 70%.

The earliest report regarding the biological function of CD38 was derived from a paper published in 1992 by States D J, et al. (States D J, Walseth T F and Lee H C. Trends Biochem. Sci. 1992, 17: 495). In this report, States D J, etc. noticed at the first time that CD38 molecule had sequence and structure identities with the Aplysia ADP-ribosyl cyclase and speculated that CD38 should have Aplysia ADP-ribosyl cyclase activity, and catalyze the conversion of $NAD^+$ into cADPR, while cADPR, as a second messenger in cells, involved in $Ca^{2+}$ mobilization; therefore, CD38 is also called ADP-ribosyl cyclase/cyclic ADP-ribose hydrolase 1 (ADPR1). Other subsequent studies also confirmed this speculation and found that CD38 protein molecules also have dehydrogenase activity, which can further catalyze cADPR into ADPR (Howard M et al. Science. 1993; 262: 105; Summerhill R J, Jackson D G, Galione A. FEBS Lett. 1993, 335:231-3; Prasad G S et al., Nature Structural Biology 1996, 3:957-964). Therefore, CD38 has the activities of bifunctional enzymes, and the active sites of these bifunctional enzymes located in the extracellular membrane structural area. The study regarding CD38 molecular structure and enzymatic activity and function thereof refers to a review (Mehta K, Shahid U and Malavasi F: Human CD38, a cell-surface protein with multiple function. FASEB J. 1996, 10; 1408-1417; George Shubinsky, Michael Schlesinger: The CD38 lymphocyte differentiation marker: new insight into its ectoenzymatic activity and its role as a signal transducer. Immunity 1997, 7:315-324).

CD38(T10) antigen was earliest discovered and reported by Feinnerz E and colleagues in 1980, they observed that the normal thymus cell and T-lymphoma cell line MOLT-4 originating from human can express an antigen specifically bound by a monoclonal antibody code-named OKT10, the antigen was called T10 at that time (Feinnerz E et al. PNAS 1980, 77:1588-1592). Other studies since then have demonstrated that CD38(T10) antigen was widely expressed in other human cells such as B-lymphocytes, macrophages, dendritic cells, platelets, bone marrow plasma cells and other blood and lymphoid cells except T-lymphocytes; In addition, different levels of CD38 (T10) antigens were also expressed in other tissue cells such as nerve cells and glial cells in the central nervous system, peripheral nerve cells, islet cells in the pancreas, osteoclasts in bone tissue, skeletal muscle cells, cardiomyocytes, and bronchial epithelial cells (See the following review: Mehta K, Shahid U and Malavasi F: Human CD38, a cell-surface protein with multiple function. FASEB J 10, 1408-1417).

However, compared with other tissue cells, CD38 antigen was expressed in the highest level in multiple myeloma (MM) and B-lymphoma. Therefore, CD38 antigen has been considered as an ideal target for the treatment of multiple myeloma and B-lymphoma since the early 1990s, and there have been many studies and reports successively on the treatment of multiple myeloma and B-lymphoma in animals in vivo or in vitro with monoclonal antibodies targeting CD38 antigen.

Stevenson F K et al. reported in 1991 that a human-mouse chimeric antibody from genetically engineered OKT10 can kill lymphoma cells with positive CD38 expression through antibody-dependent cellular cytotoxicity (ADCC) in vitro (Stevenson F K et al., Blood. 1991, 7:1071-1079).

Goldmacher V S et al. reported in 1994 that an antibody-drug conjugate was obtained with immunotoxin by coupling ricin to mouse anti-human CD38 monoclonal antibody HB7, the antibody-drug conjugate exhibited stronger activity killing positive CD38 expressing tumor cells in vitro (Goldmacher V S et al., Blood. 1994, 84:3017-25).

Ellis J H et al. reported in 1995 that another humanized antibody from genetically engineered mouse anti-CD38 monoclonal antibody AT13/5 had stronger ADCC activity than its predecessor (Ellis J H et al., J Immunol. 1995, 155:925-37).

However, these early findings have not subsequently been successfully transformed into useful clinical applications or entered clinical studies.

Multiple myeloma is a malignant plasma cell disease characterized by the latent accumulation in bone marrow of secretory plasma cells with a low proliferation and an extended life span. The disease can result in symptoms such as hypercalcemia, renal impairment, destruction of adjacent bone marrow tissue, and anemia. Before 2015, the main therapies for multiple myeloma include chemotherapy drugs such as Vincristine, Cyclophosphamide, Melphalan, Adriamycin, and Immunomodulators (IMiDs), Proteasome Inhibitors (PIs), Bisphosphonates, and hormones such as Prednisone, Dexamethasone and autologous stem cell transplantation.

Among them, the representative drugs of Immunomodulators are Thalomid (generic name: Thalidomide, approved by U.S. FDA in July 1998), Revlimid (generic name: lenalidomide, approved by U.S. FDA in December 2005), and Pomalyst (generic name: Pomalidomide, approved by U.S. FDA in February 2013) developed and launched successively by Celgene, USA.

The representative drugs of Proteasome Inhibitors are Velcade (generic name; Bortezomib, approved by U.S. FDA in May 2003) developed by Takeda/Millennium, Japan, and Kyprolis (generic name: Carfilzomib, approved by U.S. FDA in July 2012) developed by Onyx, USA. The representative drugs of Bisphosphonates are Aredia (generic name: Pamidronate, approved by U.S. FDA in October 1991) and Zometa (generic name: Zoledronic, approved by U.S. FDA in August 2001) successively developed by Novartis.

The complete Response Rate (CRR) of the combination of these drugs is generally only 5%, the Median Survival Time (MST) of patients is generally 36-48 months after the first diagnosis. As a result, new and more effective drugs for the treatment of multiple myeloma are urgently being sought.

In November 2015, the world's first anti-CD38 monoclonal antibody drug Daratumumab was approved by FDA for the treatment of patients with multiple myeloma ever received at least three times treatments, including Bortezomib, Lenalidomide or both at the same time and development of multi-drug resistance. The field of the treatment of multiple myeloma stepped into a new era of revolutionary significance, and a monoclonal antibody targeted therapy.

Daratumumab, a brand name Darzalex, was developed by Janssen Biotech, a subsidiary of Johnson & Johnson in the US, and Genmab of Denmark. Daratumumab is a fully human IgG1/kappa monoclonal antibody, specifically recognizing and binding human CD38 antigen. It was originally derived from a human CD38 monoclonal antibody code-named 005 developed by Genmab (de Weers et al. J Immunol 2001; 186:1840-8; PCT application No.: PCT/DK2006/000166, American Patent No.: U.S. Pat. No. 7,829,673B2). Preliminary non-clinical study results showed that Daratumumab/005 could rapidly kill CD38 antigen-positive tumors such as myeloma by multiple mechanisms, including complement-dependent cytotoxicity (CDC), antibody-dependent cell-mediated cytotoxicity (ADCC), antibody-dependent cell-mediated phagocytosis (ADCP), and apoptosis. In addition, Daratumumab/005 can also inhibit ADP-ribosyl cyclase mediated by CD38 and thus play a role.

In 2011, Johnson & Johnson and Genmab reached an agreement of clinical cooperation in the development of Daratumumab. In 2013, Daratumumab achieved Fast Track Designation and Breakthrough Therapy Designation by the U.S. FDA because of its good single-drug activity in a clinical trial for the treatment of myeloma. In November 2015, Daratumumab was quickly approved to launch marketing by the U.S. FDA based on the results of two phase I/II clinical trials named GEN501 (Lokhorst H M et al., N Engl J Med. 2015, 373:1207-19) and SIRIUS (Lonial S et al., Lancet. 2016, 387:1551-60), and used as a four-line therapy for patients with multiple myeloma ever received at least three times treatments including Bortezomib, Lenalidomide or both at the same time and development of multi-drug resistance. During GEN501 and SIRIUS clinical trials, the results demonstrated that the objective response rate (ORR) and the median progression-free survival (PFS) of Daratumumab treatment group with an injection dose of 16 mg/kg body weight had significantly improved.

After Daratumumab's launching, two Phase III clinical studies named POLLUX and CASTOR were developed by Johnson & Johnson/Genmab. Wherein POLLUX was to evaluate the clinical efficacy of the combination of Daratumumab, Lenalidomide, and Dexamethasone as a third-line therapy for the treatment of myeloma. A total of 569 patients with myeloma were enrolled in this study, including 286 patients in the combination group of Daratumumab, Lenalidomide, and Dexamethasone (treatment group), and 283 patients in the combination group of Lenalidomide and Dexamethasone (control group). The study results showed that proportion of patients with progression-free survival (PFS) of the treatment group combined with Daratumumab at 12 months was 83.2%, ORR was 92.9%, both are significantly higher than the control group (PFS proportion was 60.1%, ORR was 76.4%) (Dimopoulos et al. POLLUX Investigators, N Engl J Med. 2016, 375:1319-31).

CASTOR was to evaluate the clinical efficacy of the combination of Daratumumab, Bortezomib, and Dexamethasone as a third-line therapy for the treatment of myeloma. A total of 498 patients with myeloma were enrolled in this study, including 251 patients in the combination group of Daratumumab, Lenalidomide, and Dexamethasone (treatment group), and 247 patients in the combination group of Bortezomib and Dexamethasone (control group). The study results showed that the proportion of patients with progression-free survival (PFS) of the treatment group combined with Daratumumab at 12 months was 60.7%, ORR was 82.9%, both are significantly higher than the control group (PFS proportion was 26.9%, ORR was 63.2%) (Palumbo A et al., CASTOR Investigators. N Engl J Med. 2016, 375:754-66).

Combination of Daratumumab, lenalidomide, and Dexamethasone and combination of Daratumumab, Bortezomib, and Dexamethasone were approved as a third-line therapy for the treatment of myeloma by the U.S. FDA in November 2016 based on the above two Phase II clinical trials POLLUX and CASTOR.

Combination of Daratumumab, Pomalidomide, and Dexamethasone was approved as a second-line therapy for the treatment of myeloma by the U.S. FDA in June 2017 based on the clinical trial results code-named EQUULEUS (MMY1001). This study showed that the ORR was 60%, median PFS was 8.8 months, and median overall survival was 17.5 months in a combination of Daratumumab, Pomalidomide, and Dexamethasone for the treatment of myeloma (Ajai Chari, et al, EQUULEUS; MMY1001 Investigators: Blood. 2017, 130: 974-981).

The U.S. FDA approved a combination of Daratumumab, Bortezomib, Melphalan, and Prednisone in May 2018 for the first-line treatment of newly diagnosed myeloma patients who have not received high-dose chemotherapy and autologous stem cell transplantation (ASCT) based on a clinical trial study result code-named ALCYONE. 706 patients with myeloma were enrolled in ALCYONE study, and the results showed that that the proportion of patients with Progress-free survival(PFS) of the treatment group combined with Daratumumab at 18 months was 71.6%, ORR was 90.9%, both significantly higher than the control group (PFS proportion was 50.2%, ORR was 73.9% (Mateos M-V et al., ALCYONE Investigators. N Engl J Med. 2018, 378:518-528).

As a result, from firstly approved by the U.S. FDA in November 2015, in just three years, Daratumumab has been gradually promoted from a single-drug four-line therapeutic drug to a first-line therapeutic drug, and quickly became a best-selling blockbuster drug on the market. Daratumumab is the only anti-CD38 monoclonal antibody in the world that has been approved for marketing. The other anti-CD38 monoclonal antibodies entered clinical trials currently are a human-mouse chimeric antibody SAR650984 (Isatuximab), developed by Sanofi/Immungen, and a fully human monoclonal antibody MOR202 screened from the Phage-Display antibody library, developed by MorphoSys, a German pharmaceutical company. The main clinical indications for these antibodies are also myeloma.

In China, the mainly available therapeutic drugs for myeloma are imported Bortezomib/Velcade, lenalidomide, etc. With the patent expiration of Bortezomib/Velcade and other drugs, dozens of domestic enterprises have been developing their generic drugs. Among them, Bortezomib generic drugs developed by Qilu Pharmaceutical, Chia Tai Tianqing, and Jiangsu Hansoh Pharma, have recently been approved by the China Food and Drug Administration (CFDA) to launch for the treatment of myeloma. However, the monoclonal antibody drugs targeting CD38, only Daratumumab from Johnson & Johnson, and SAR650984 (Isatuximab) from Sanofi, as individual imported products, has completed clinical trial application or just entered the clinical trials in domestic, So far, no CD38 monoclonal antibody independently developed by domestic enterprises has entered the clinical trial application or clinical trial stage.

Based on the large number of patients with myeloma at home and abroad, there is a severe shortage of drugs for the treatment of myeloma, especially antibody drugs. Therefore, it is of great significance and necessity to research and develop new drugs for the treatment of myeloma, especially monoclonal antibodies targeting CD38 antigen.

Although Daratumumab has been widely praised by clinicians, patients and the market since its launching, it still has many defects and deficiencies, including at least the following:

1) When patients receive intravenous infusion of Daratumumab, there is a high rate of clinical adverse reactions, and the administration time is relatively long. For example, the first intravenous infusion takes 8 hours, and the second injection also takes 5-6 hours, and patients need to receive treatment once a week in the first course of 8 weeks.

2) Some myeloma patients have no clinical response to Daratumumab treatment; Others continued to progress or developed resistance after treatment with Daratumumab; The causes and mechanisms of patients' resistance or failure to Daratumumab treatment are not yet known.

3) Daratumumab does not recognize monkey CD38 antigen, which limits its preclinical efficacy, pharmacological toxicology, and other research and development applications in monkeys and other non-human primates used as a single drug or in combination with other drugs.

Based on a 70% identity between the amino acid sequences of mouse CD38 and human CD38, it is speculated in theory that a new monoclonal antibody with a different epitope on CD38 can be prepared or developed with the traditional technique of immunizing mice with antigen protein and hybridomas. From them, it is expected that a drug with greater bioactivity or safety than Daratumumab or other CD38 monoclonal antibodies that are undergoing clinical research, which is currently on the market, may be developed. These new monoclonal antibodies can be used as a single drug or sequentially or combined with other myeloma drugs currently on the market, such as Bortezomib, Lenalidomide, etc. to treat tumors with CD38 high expression such as myeloma and lymphoma.

SUMMARY

A technical problem to be solved in the present invention is to provide a novel antibody or a derivative thereof such as a Fab fragment, a single-chain antibody, etc., with the antigen-binding site/epitope different from Daratumumab, binding human and monkey CD38 antigens, and with the bioactivity capable of killing tumors in vivo and in vitro with CD38 antigen high expression.

A second technical problem to be solved in the present invention is to provide a DNA molecule or gene coding the above antibody.

A third technical problem to be solved in the present invention is to provide a pharmaceutical compound or a pharmaceutical composition comprising the above antibody.

A fourth technical problem to be solved in the present invention is to provide a use of the pharmaceutical compound or the pharmaceutical composition comprising the above antibody for the treatment of tumors with positive CD38 antigen high expression.

A fifth technical problem to be solved in the present invention is to provide a preparation method of the above antibody.

To resolve the above technical problems, the present invention adopts the following technical solutions:

In one aspect, the present invention provides a novel anti-CD38 monoclonal antibody or a derivative thereof, with antigen-binding site/epitope different from Daratumumab. The monoclonal antibody or the derivative thereof comprises a first variable region and a second variable region, wherein the first variable region is an antibody light chain variable region comprising antigen complementarity-determining regions CDR1, CDR2 and CDR3 having amino acid sequences as set forth in SEQ ID NO: 3, SEQ ID NO: 4 and SEQ ID NO: 5, respectively; and wherein the second variable region is an antibody heavy chain variable region comprising antigen complementarity-determining regions CDR1, CDR2 and CDR3 having amino acid sequences as set forth in SEQ ID NO: 8, SEQ ID NO: 9 and SEQ ID NO: 10, respectively.

The antibodies include a human-mouse chimeric antibody, a half chimeric/half humanized antibody, and a humanized monoclonal antibody; the derivatives include a Fab fragment of an antibody, a single-chain Fab fragment, an Fv fragment, a single-chain antibody, a bispecific antibody, an antibody-drug conjugate (ADC), chimeric antigen receptor T-cell (CAR-T), etc.

As a preferred technical solution, the first variable region is an antibody light chain variable region having an amino acid sequence as set forth in SEQ ID NO: 2; and the second variable region is an antibody heavy chain variable region having an amino acid sequence as set forth in SEQ ID NO: 7.

As a preferred technical solution, the first variable region is an antibody light chain variable region having an amino acid sequence as set forth in SEQ ID NO; 11; and the second variable region is an antibody heavy chain variable region having an amino acid sequence as set forth in SEQ ID NO: 12 or SEQ ID NO: 7.

As a preferred technical solution, the antibody or derivative thereof comprises the antibody light chain variable region, a human antibody light chain constant region, the antibody heavy chain variable region, and a hinge region of a human antibody heavy chain constant region, CH1 region, CH2 region, and CH3 region.

As a preferred technical solution, the human antibody light chain constant region is a kappa chain or a lambda chain of a human antibody; the human antibody heavy chain constant region is a human IgG1, IgG2, IgG3, and IgG4 isotype; wherein the IgG1 isotype is more preferred.

In a second aspect, the present invention provides a DNA molecule or gene coding the above antibody or derivative thereof, wherein a nucleotide sequence of the antibody light chain variable region is set forth in SEQ ID NO: 1 or SEQ ID NO: 13, and a nucleotide sequence of the antibody heavy chain variable region is set forth in SEQ ID NO: 6 or SEQ ID NO: 14.

In a third aspect, the present invention provides an expression vector comprising a nucleotide sequence coding the DNA molecular/gene of the above antibody or derivative thereof and an expression regulatory sequence operably linked to the nucleotide sequence.

In a fourth aspect, the present invention provides a recombinant host cell transfected with the above expression vector. The recombinant host cell or a progeny cell thereof expresses the above antibody or derivative thereof. The antibodies include a humanized monoclonal antibody; the derivatives comprise a Fab fragment of an antibody, a single-chain antibody, a bispecific antibody, etc.

In a fifth aspect, the present invention provides a pharmaceutical compound or a pharmaceutical composition comprising a pharmaceutically effective amount of the antibody or derivative thereof and a pharmaceutically accepted carrier.

In a sixth aspect, the present invention provides a use of the above pharmaceutical compound or the pharmaceutical composition for the preparation of a medicament for the treatment of tumors, particularly for the tumors with positive CD38 expression. The preferred tumors with positive CD38 expression include human myeloma, human lymphoma (B-lymphoma), etc. A specific example of the present invention depicts a use of the antibody in inhibiting the growth of a human B-lymphoma Raji with positive CD38 high expression in vivo.

As another preferred technical solution, the anti-CD38 antibody in the present invention used for the tumors with positive CD38 expression can be more consideration wild-type or genetically engineered constant regions of human IgG1 or IgM isotype antibody, to maintain or increase antibody-dependent cellular cytotoxicity (ADCC) or complement-dependent cytotoxicity (CDC), further achieve the effect of a stronger killing of tumor tissues or cells. The wild-type or genetically engineered constant regions of human IgG1 or IgM isotype antibody can be cloned or synthesized in vitro, respectively, by genetic engineering technology known to the skilled in the art.

The CD38 antibody or the derivative thereof in the present invention can be used as a targeting carrier to graft or wrap with other anti-tumor drugs or toxins to form antibody-drug conjugates (ADC), targeted together to the tumor tissues and achieved a better effect of killing tumor. The grafting or wrapping method of antibody and drugs or toxins can take the conventional techniques known to people in this art.

As another preferred technical solution, the anti-CD38 antibody or derivative thereof in the present invention can be administered sequentially or in combination with anti-tumor angiogenesis drugs or inhibitory immune checkpoint molecules to treat tumors with positive CD38 expression.

Wherein the preferred anti-tumor angiogenesis drugs administered sequentially or in combination with the anti-CD38 antibody or derivative thereof in the present invention were the macromolecular biological drugs targeting vascular endothelial growth factor (VEGF) or its receptor (VEGF-R) or small molecular chemical drugs. The preferred targeting VEGF and/or VEGF-R macromolecular biological drugs comprise anti-VEGF monoclonal antibody Bevacizumab (brand name: Avastin), anti-VEGF monoclonal antibody Fab fragment Ranibizumab (brand name: Lucentis); anti-VEGFR2 monoclonal antibody Ramucirumab (brand name: Gyramza) and anti-VEGF monoclonal antibody code-named hPV19 (under development in Suzhou Stainwei Biotech Inc., see Chinese patent document: ZL 201210540692X, patent title: monoclonal antibody for antagonizing and inhibiting the binding of vascular endothelial growth factor to its receptor, as well as coding sequence and use; American granted patent document: U.S. Pat. No. 9,580,498B2); VEGFR-Fc fusion protein drugs such as Albercept (brand name: Eylea), Conbercept, etc. The preferred targeting VEGFR small molecular chemical drugs comprise Sunitinib, Sorafenib, Apatinib, Pazopanib, etc.

The preferred target inhibitory immune checkpoint molecules used sequentially or in combination with anti-CD38 antibody or the derivative thereof in the present invention include anti-CTLA4 (Cytotoxic T-lymphocyte Antigen-4) monoclonal antibody Ipilimumab (brand name: Yervoy); anti-PD-1 (programmed death protein-1) antibody Nivolumab (brand name: Opdivo), Pembrolizumab (brand name: Keytruda), code-named hAB21 (under development in Suzhou Stainwei Biotech Inc., See PCT patent application document: PCT/CN2017/089282, monoclonal antibody antagonizing and inhibiting binding between human PD-1 antigen and ligand thereof, preparation method thereof and application thereof); anti-PD-L1 monoclonal antibody drugs include Atezolizumab (brand name: Tecentriq), Avelumab (brand name: Bavencio), Durvalumab (brand name: Imfinzi), etc.

As another preferred technical solution, the anti-CD38 antibody in the present invention can be firstly prepared into chimeric antigen receptor T-cell (CAR-T), then introduced into the immune cells isolated from peripheral blood of tumor patients, such as T-lymphocytes, after culturing and amplification in vitro, these lymphocytes recognizing CD38 antigen were injected back into the body to achieve the effect of treating the tumor by targeting tumors with CD38 high expression. The preparation of anti-CD38 antibody in the present invention into chimeric antigen receptor T-cell (CAR-T) can take conventional techniques known to a person skilled in the art.

In a seventh aspect, the present invention provides a method for preparing the above antibody or derivative thereof, and the method comprises the following steps:
 e) providing an expression vector comprising the above DNA sequence and an expression regulatory sequence operably linked to the DNA sequence;
 f) transfecting a host cell with the expression vector of step a);
 g) culturing the host cell from step b) under conditions suitable for the expression of the antibody; and
 h) isolating, purifying, and collecting the antibody from a host cell culture medium.

The term "monoclonal antibody (mAb)" used herein refers to an immunoglobin obtained from a clonal cell, with the same structure and chemical characteristics and specific to a single antigenic determinant. The monoclonal antibody is different from a regular polyclonal antibody preparation (usually having different antibodies directed against different determinants). Each monoclonal antibody is directed against a single determinant of an antigen. In addition to its specificity, the monoclonal antibody is also advantageous because it is cultured from hybridoma or recombinant engineering cells and will not be mixed with other immunoglobulins. The modifier "monoclonal" indicates that the antibody's properties are achieved from a homogeneous population of antibodies, which should not be interpreted as any special method that needs to be used for the production of antibodies.

The term "humanized monoclonal antibody" as used herein refers to that all or most of the amino acid sequences of the murine monoclonal antibodies (including the framework region sequence in the variable region), except complementarity-determining regions (CDR) are substituted by the amino acid sequences of human immunoglobulins, to reduce the immunogenicity of the murine monoclonal antibody to the utmost extent by genetic engineering methods.

The terms "antibody" and "immunoglobulin" used herein refer to an iso-tetra proteoglycan of about 150,000 Daltons with the same structural characteristics and consist of two identical light chains (L) and two identical heavy chains (H). Each light chain is linked to the heavy chain through a covalent disulfide bond, while the same isotype heavy chains of the different immunoglobulins have a different amount of disulfide bonds. Each heavy chain and each light chain also have regularly spaced intrachain disulfide bonds. Each heavy chain has a variable region ($V_H$) at one end, followed by several constant regions. Each light chain has a variable region ($V_L$) at one end, and a constant region at the other end. The constant region of the light chain is opposite to the first constant region of the heavy chain. The variable region of the light chain is opposite to the variable region of the heavy chain. Special amino acid residues form an interface between the variable region of the light chain and the heavy chain.

The term "variable" used herein indicates that some portion of the variable region in an antibody are different in sequence, which results in binding and specificity of various specific antibodies to the specific antigens. However, variability is not evenly distributed throughout the whole antibody variable region. Instead, it concentrates on three fragments in the complementarity-determining region (CDR) and hypervariable region in the light-chain or heavy-chain variable regions. The more conservative part of the variable region is called the framework regions (FR). There are four FR regions in each variable region of the heavy-chain and light-chain of an antibody. The FR regions are roughly in a β-folded configuration and connected by three CDRs forming a connecting loop. The partial β-folded configuration can form in some cases. The CDRs in each chain are close together through the FR regions and form the antigen-binding site of the antibody together with the CDRs of another chain (see Kabat et al, NIH Publ. No. 91-3242, Vol. 1, pp. 647-669 (1991)). The antibody's constant region does not directly participate in the binding of the antibody to the antigen. Still, it exhibits different effects and functions, such as participating in antibody-dependent cellular cytotoxicity (ADCC) and complement-dependent cytotoxicity (CDC) of the antibody.

The antibody of the present invention can be usually prepared by the following methods:

Firstly, insert the gene coding the antibody in the present invention into the expression vector containing a suitable expression regulatory sequence.

The term "expression regulatory sequence" used herein usually refers to a sequence that participates in the control of the gene expression. The expression regulatory sequence includes a promoter operable linked to the target gene and a termination signal. The gene (DNA) sequence of the present invention's antibody can be encoded by the common techniques well known by the skilled in the art, such as artificial synthesis according to the protein sequences disclosed by the present invention or the PCR amplification. After that, the DNA fragments synthesized or amplified by the PCR method can be inserted into a suitable expression vector by various methods well known in the art. The expression vector used in the present invention can be available on the market and well known for those skilled in the art, such as the pCDNA3.1 expression vector from Invitrogen.

The suitable host cells for accepting the expression vector transformation generally include both prokaryotes and eukaryotes. Commonly used prokaryotes host cells include *E. coli*, and *Bacillus subtillis*, etc. Commonly used eukaryotes host cells include yeast cells, insect cells, and mammalian cells. In the present invention, the preferred host cells are mammalian, particularly Chinese hamster ovary (CHO) cells.

The host cells transfected by the expression vector are cultured under suitable conditions (e.g., culturing with a serum-free culture medium in a cell culture flask or bioreactor by adhesion to the wall or suspension). The supernatant is collected and purified by common separation steps or means well known by the skilled in the art, including protein-A affinity chromatography, ion-exchange chromatography, filtration, etc. to produce the antibodies of the present invention.

The purified antibodies of the present invention can be dissolved in an appropriate solvent such as sterile saline liquid. The solubility can be prepared between 0.01 and 100 mg/mL. The ideal final solubility can be prepared between 1 mg/ml and 20 mg/ml.

To obtain a novel murine monoclonal antibody specifically binding CD38 antigen as well as the hybridoma cell line secreting this antibody, the present invention chose recombinant human CD38 protein extracellular membrane area expressed by the mammalian cell as an immune antigen, then immunized mice to obtain the anti-CD38 protein polyclonal antibody by repeated small dose subcutaneous injection. The mice with high titers of antibody were selected to get the spleen cells, fused with a mouse myeloma cell line in vivo. After a few steps, such as drug screening and subcloning, several hybridoma monoclonal cells stably secreting the antibody of anti-human CD38 protein were established. A mouse hybridoma clone code-named m29 was tested by ELISA, flow Cytometer, and other many methods and proved that the secreted monoclonal antibody could not only specifically bind human CD38 protein and several tumor cell lines with positive CD38 expression originating from human, but also capable of killing the tumor cells with positive CD38 expression by CDC in vitro.

The gene fragments coding the heavy-chain and light-chain variable region were obtained by genetic engineering methods, etc. in the present invention. On the above basis, the expression vectors expressing the human-mouse chimeric antibody or the humanized antibody were obtained after genetic engineering. The expression vectors were transfected into Chinese hamster ovary (CHO) cells to obtain the recombinant engineering cells stably and efficiently secreting the human-mouse chimeric antibody or the humanized antibody. The recombinant engineering cells culture medium was isolated and purified to obtain a human-mouse chimeric antibody ch29 protein or a humanized antibody HH29 protein with the bioactivity.

Identification analysis in vitro by many methods, including competitive ELISA, flow cytometer, etc. showed that: the epitopes of binding the murine monoclonal antibody m29 and the human-mouse chimeric antibody thereof ch29 to CD38 antigen are different from Daratumumab. The Analysis results in vitro by direct ELISA, flow cytometer, etc. also showed that: the murine monoclonal antibody m29 and the human-mouse chimeric antibody thereof ch29 can specifically bind to recombinant monkey CD38 protein and CHO cell lines expressing CD38 recombinant gene with high affinity; in contrast, the monoclonal antibody Daratumumab only binds to human CD38 antigen but does not significantly bind to monkey CD38 antigen.

The anti-tumor effects of the murine monoclonal antibody m29 and the human-mouse chimeric antibody ch29 were tested in immunodeficient mice in vivo. The results showed that the murine monoclonal antibody m29 and the human-mouse chimeric antibody ch29 thereof after administration in vivo has obvious inhibition to the tumor growth, further the efficacy is no less than the positive control drug on the market such as Rituximab (brand name: Rituxan, a human-mouse chimeric anti-CD20 monoclonal antibody) or Daratumumab.

BRIEF DESCRIPTION OF THE DRAWINGS

FIG. 1 is a schematic diagram of the amino acid sequences comparison analysis of human CD38 protein and mouse CD38 protein in Example 1 of the present invention.

FIGS. 4A-4C are schematic diagrams of the representative results of determining and analyzing the binding of the supernatant sample of the mouse hybridoma cell line m29 to human tumor cell lines with positive CD38 expression by flow cytometer in Example 4 of the present invention; the negative control sample is a non-related mouse hybridoma mAB21 (mouse anti-human PD-1 monoclonal antibody); wherein FIG. 4A is a detecting result diagram of human B-lymphoma cell line Daudi by flow cytometer;

FIG. 4B is a detecting result diagram of human myeloma cell line RPMI-8226 by flow cytometer;

FIG. 4C is a detecting result diagram of human T-lymphoma cell line MOLT-4 by flow cytometer;

FIGS. 5A-5B are representative result diagrams of determining and analyzing the binding of the mouse monoclonal antibody m29 sample and the positive control sample Daratumumab to CHO cells transfected and expressed with human CD38 gene (CHO-hCD38); the negative control sample is the non-related mouse hybridoma mAB21 (mouse anti-human PD-1 monoclonal antibody) or a humanized monoclonal antibody hAB21; Wherein FIG. 5A is a detecting result diagram of the mouse monoclonal antibody m29 by flow cytometer;

FIG. 5B is a detecting result diagram of the positive control sample Daratumumab by flow cytometer.

FIGS. 6A-6B are schematic diagrams of detecting the competitive binding of purified mouse monoclonal antibody m29 sample and Daratumumab to CD38 by ELISA in Example 6 of the present invention; the negative control sample is the non-related humanized monoclonal antibody sample hPV-19 (anti-VEGF monoclonal antibody); Wherein FIG. 6A is a result diagram of the competitive binding of mouse monoclonal antibody m29, Daratumumab, and Biotin-labeled Daratumumab sample to CD38;

FIG. 6B is a result diagram of the competitive binding of mouse monoclonal antibody m29, Daratumumab, and Biotin-labeled monoclonal antibody m29 to CD38;

FIGS. 7A-7B are variable region amino acid sequences comparison analysis diagrams of the mouse monoclonal antibody m29 and Daratumumab in Example 7 of the present invention, wherein FIG. 7A is a light chain variable region amino acid sequences comparison analysis diagram, the different amino acids between m29 and Daratumumab are marked by "X", the amino acid sequence areas of CDR1, CDR2, and CDR3 of the light chain variable region are marked in box.

FIG. 7B is a heavy chain variable region amino acid sequences comparison analysis diagram; the different amino acids between m29 and Daratumumab are marked by "X", the amino acid sequence areas of CDR1, CDR2, and CDR3 of the heavy chain variable region are marked in box.

FIGS. 8A-8D are the representative result diagrams of determining and analyzing the binding of the mouse monoclonal antibody m29 sample, the human-mouse chimeric antibody ch29G, and the positive control sample Daratumumab or Rituximab (Rituxan, a human-mouse chimeric anti-CD20 monoclonal antibody) to human tumor cell lines; wherein FIG. 8A is a detecting result diagram of human B-lymphoma cell line Raji by flow cytometer;

FIG. 8B is a detecting result diagram of human myeloma cell line RPMI-8226 by flow cytometer;

FIG. 8C is a detecting result diagram of human T-lymphoma cell line MOLT-4 by flow cytometer;

FIG. 8D is a detecting result diagram of human T-lymphoma cell line Jurkat by flow cytometer;

FIG. 10 is the binding result diagrams of detecting the binding of the mouse monoclonal antibody m29 sample, the human-mouse chimeric antibody ch29G sample, and the control sample Daratumumab to CHO cells stably transfected and expressed with wild-type human CD38 (CHOhCD38/wild-type) or CHO cells stably transfected and expressed with CD38 with $S_{274F}$ mutation (CHO-hCD38/$S_{274F}$ mutation) in Example 11 of the present invention; the negative control sample is a non-related humanized monoclonal antibody hAB21 (anti-human PD-1 monoclonal antibody). Wherein

FIG. 11A is the amino acid sequences comparison analysis result diagram of human CD38 protein, chimpanzee CD38 protein, and cynomolgus macaque CD38 protein.

FIGS. 13A-13D are CDC activity diagrams of detecting and analyzing the human-mouse chimeric antibody ch29G sample, Daratumumab, and the positive control sample Rituximab (human-mouse chimeric anti-CD20 monoclonal antibody); the source of complement is human serum, and the negative control sample is a non-related humanized hPV19 Mab (anti-VEGF Mab) in Example 14 of the present invention, wherein FIG. 13A is a CDC detecting result diagram targeting human B-lymphoma cell line Daudi;

FIG. 13B is a CDC detecting result diagram targeting human B-lymphoma cell line Raji;

FIG. 13C is a CDC detecting result diagram targeting human T-lymphoma cell line MOLT-4;

FIG. 13D is a CDC detecting result diagram targeting human T-lymphoma cell line Jurkat.

FIGS. 14A-14B are the anti-tumor efficacy result diagrams in vivo of detecting the mouse monoclonal antibody m29 in Raji tumor model inoculating human B-lymphoma cells subcutaneously in nude mouse in Example 17 of the present invention; wherein FIG. 14A is a schematic diagram of average tumor growth volume ten days before inoculating; FIG. 14B is a schematic diagram of the average growth volume of the tumor at the later stage of inoculating.

DETAILED DESCRIPTION OF THE EMBODIMENTS

Figure 2A:
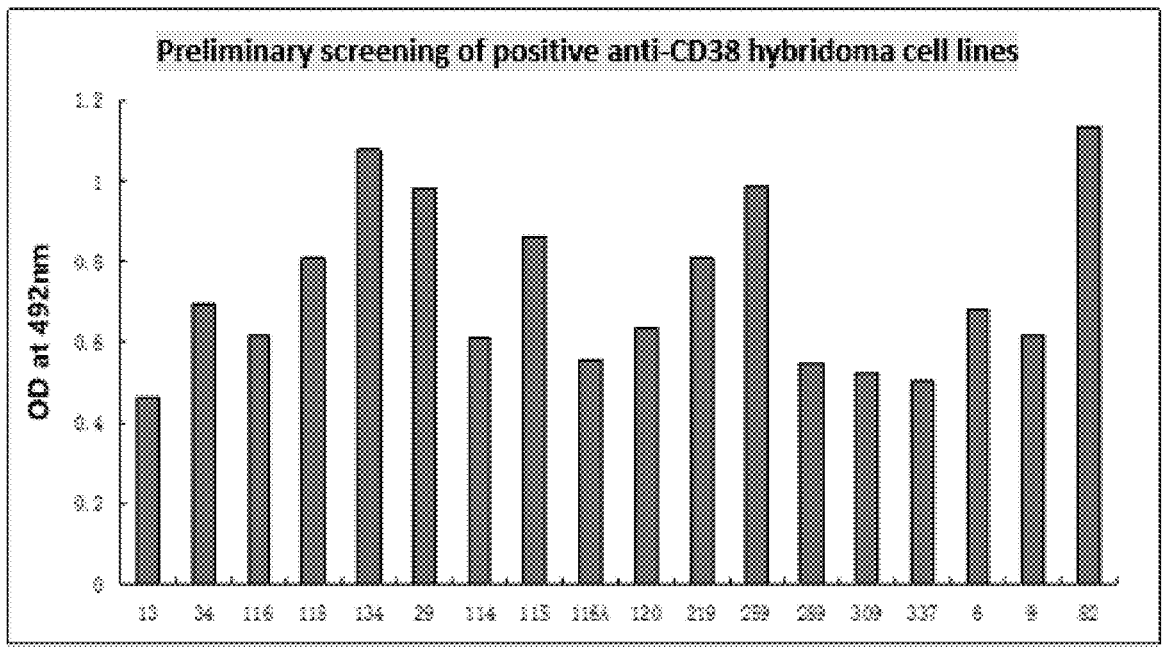
FIG. 2A is a schematic diagram of the code-names and testing OD values of various hybridoma cell lines secreting anti-CD38 antibody screened by ELISA in Example 1 of the present invention.

The present invention will be further described by reference to the following examples, which are illustrative only and are not intended to limit the present invention.

Tumor cell lines and DNA primers used in the present invention are shown in Table 1 and Table 2, respectively:

TABLE 1

Names and characteristics of tumor cell lines used in the present invention

| Names of cell lines (ATCC code-name) | Origin of tumors | Surface antigen characteristics | Main references |
|---|---|---|---|
| Daudi (CCL-213) | B-lymphoblast, Burkitt's lymphoma patients | CD20$^+$, CD38$^+$, sIgM$^+$ | Klein E, et al. Surface IgM-kappa specificity on a Burkitt lymphoma cells. Cancer Res. 28: 1300, 1968 |
| Raji (CCL-86) | B-lymphoblast Burkitt's lymphoma patients | CD38$^+$, CD20$^+$, sIgM$^-$ | Pulvertaft JV. Cytology of Burkitt's tumour (African lymphoma) Lancet 1: 238-240, 1964 |
| RPMI8226 (CCL-155) | B-lymphoblast myeloma patients | CD19$^-$, CD20$^+$, CD28$^+$, CD38$^+$, CD49$^+$, sIgM$^-$ | Matsuoka Y, et al. Proc. Soc. Exp. Biol. Med. 125: 1246-1250 1967 |
| Molt-4 (CRL-1582) | T-lymphoblast, acute lymphoblastic leukemia patients | CD3A (26%), CD3B (33%), CD3C (34%), CD4 (55%) | Minowada J, et al. J. Natl. Cancer Inst. 49: 891-895, 1972 |
| Jurkat (TIB-152) | T-lymphoblast, acute T-cell leukemia patients | CD3$^+$, CD4$^+$ | Gillis S, Watson J.J. Exp. Med. 152: 1709-1719, 1980 |

TABLE 2

Names and sequences of primers used in the present invention

| Names of primers | Sequences |
|---|---|
| 1. huCD38F-HindIII-2 | TTGTAAGCTTGCCGCCACCATGGCTAACTGCG AGTTCTCC (SEQ ID NO: 15) |
| 2. huCD38-S274F-R1 | CTTATCGGGCCTATAGATATTTTTGCAGAAGA ACTGGATGTTCCGCTTGCTGATGATGC (SEQ ID NO: 16) |
| 3. huCD38-S274F-R2-XhoI | TGGTCTCGAGTCAGATCTCGGAGGTGCAGCTG GAGTCTTCGGGGTTCTTCACGCACTGTAAAAA CTTATCGGGCCTATAGATATT (SEQ ID NO: 17) |
| 4. mKaRT | TGTCGTTCACTGCCATCA AT (SEQ ID NO: 18) |
| 5. mGaRT | GCAAGGCTTACAACCACAATC (SEQ ID NO: 19) |
| 6. mIgLF1 | GACATTGTGATGWCMCA (W = A or T, M = A or C) (SEQ ID NO: 20) |
| 7. mIgLCR440 | CTGAGGCACCTCCAGATGTT (SEQ ID NO: 21) |
| 8. mIgHset1 | CARCTGCARCARYCT (G, R = A or G, Y = C or T) (SEQ ID NO: 22) |

TABLE 2-continued

Names and sequences of primers used in the present invention

| Names of primers | Sequences |
|---|---|
| 9. mIgHCRA135 | GTGCTGGAG GGG ACA GTC ACT (SEQ ID NO: 23) |

Example 1. Establishment and Screening Identification of Mouse Hybridoma Cell Line Secreting Anti-Human CD38 Antibody 1.1 Amino Acid Sequences Comparison Analysis of Human CD38 Protein and Mouse CD38 Protein.

The comparison analysis of amino acid sequences of human CD38 protein and mouse CD38 protein was shown in FIG. 1 (amino acid sequences of the transcellular membrane regions were marked in box and italics). As shown in FIG. 1, there is only 59% identity in amino acid sequences between human CD38 protein and mouse CD38 protein; therefore, it is speculated that mouse anti-human CD38 monoclonal antibodies targeting different binding regions or amino acid binding sites should be prepared by the traditional immunizing mice with antigen protein and hybridoma preparation techniques. It is expected that the bioactivity and efficacy of these anti-human CD38 monoclonal antibodies, in vitro and in vivo, may be different or even better than those of existing CD38 monoclonal antibodies, such as Daratumumab, may be due to different antigen-binding sites/epitopes from the existing CD38 monoclonal antibodies such as Daratumumab. These novel CD38 monoclonal antibodies recognizing new sites as pharmaceutical components, on the one hand, can be administered sequentially or combined with the myeloma therapeutic drugs on the market such as Bortezomib, Lenalidomide to enhance the therapeutic efficacy of myeloma; on the other hand, they are also expected to be developed for the treatment of other positive CD38 expression tumors such as B-lymphoma, T-lymphoma, etc.

Therefore, the present invention developed and prepared the novel anti-CD38 antibodies; the specific preparation steps were as follows:

1.2 Establishment and Screening Identification of Mouse Hybridoma Cell Lines Secreting Anti-CD38 Antibody Step 1: Origin of Recombinant Human CD38 Protein (Immunizing Antigen) and Animals Immunization In the example of the present invention, immunizing antigen is the recombinant human CD38 extracellular membrane protein expressed by a mammal (Human CD38 Protein-His Tag, Sino Biological Inc. Catalog: 10818-H08H). The recombinant human CD38 protein was mixed with Complete Freund's Adjuvant (Sigma, USA) and injected Balb/c mice subcutaneously at multipoint (100 μl/mouse, 10 μg CD38 protein each time). Three weeks after the first immunization, CD38 protein was mixed with Incomplete Freund's Adjuvant and immunized mice subcutaneously at multipoint at a dose of 10 μg/mouse; after that, the mice were boosted two to three times every two weeks in the same way; one week after the third booster immunization, the serum was collected from the mice tail vein blood, then the anti-CD38 antibody titers in mice serum were detected by ELISA method using 96-well plates coated with the recombinant human CD38 protein.

The ELISA detecting steps were as follows: the 96-well plates were coated with the recombinant human CD38 protein (2 μg/ml, pH 9.6, 0.1 M NaHCO$_3$ solution), incubated at 37° C. for 2 hours, 2% Bovine Serum Albumin (BSA) was added and sealed overnight at 4° C. The next day, the coated plates were washed with PBS-0.1% Tween20 solution, followed by the addition of immunized mice serum samples with serial dilution (an unimmunized mice serum as a negative control) and incubated at 37° C. for 2 hours; after washing with PBS-0.1% Tween20 solution, the HRP-Goat anti-Mouse IgG (Sigma, USA) was added and incubated at 37° C. for 1 hour; after washing with PBS-0.1% Tween20 solution again, the substrate solution o-Phenylenediamine (OPD)-0.1% H$_2$O$_2$ was added for staining about 10-15 minutes, then 0.1M HCl solution was added to quench the reaction. Thereafter, the OD values at 492 nm were read in a multimode reader (PerkinElmer Victor X3). The mouse splenocytes with relatively high titers were collected for the fusion of the next step.

Step 2: Cell Fusion

After three to four days of the last immunization (the fourth booster immunization), the splenocytes suspension of mice were prepared in a sterile condition, fused with the mouse SP2/0 myeloma cells (purchased from Cell Center of Shanghai Institute of Life Sciences, Chinese Academy of Sciences) at a ratio of 5:1 or 10:1 at 50% PEG-1000 (Sigma, USA) based upon standard protocols (Kohler G and Milstein C: Nature 1975; 256:495-497): 1 mL PEG was added slowly within 60 seconds, reacted for 90 seconds, terminated the reaction with the serum-free RPMI-1640 culture medium, centrifuged 10 minutes with 1000 rpm to remove the supernatant; the precipitated cells under the centrifugation were obtained and adjusted the cells density to 1×10$^6$/ml with RPMI 1640-10% Y, FCS culture medium containing 10% HAT (H for hypoxanthine, A for aminopterin, T for thymidine nucleoside, Sigma, USA), then added into 96-well flat-bottom cell culture plates (200 ul/well), and incubated in an incubator containing 5% CO2 (Thermo, USA) at 37° C. for two to three weeks.

Step 3: Screening of Mouse Hybridoma Cell Lines with Positive Anti-CD38 Antibody Secretion by ELISA The same ELISA with the above anti-CD38 antibody titers detecting method of the serum of mouse hybridoma cell lines was used to determine anti-CD38 antibody in mouse hybridoma cell culture supernatant.

The ELISA detecting steps were as follows: the 96-well plates were coated with the recombinant human CD38 protein (2 μg/ml, pH 9.6, 0.1 M NaHCO$_3$ solution) at 37° C. for 2 hours, 2% Bovine Serum Albumin (BSA) was added and sealed overnight at 4° C. The next day, the coated plates were washed with PBS-0.1% Tween20 solution, followed by the addition of the hybridoma cell culture supernatant to be detected (an unfused SP2/0 myeloma cell culture supernatant as a negative control, serum sample of mice immunized with CD38 antigen as a positive control) and incubated at 37° C. for 2 hours; after washing with PBS-0.1% Tween20 solution, the HRP-Goat anti-Mouse IgG (Sigma, USA) was added and incubated at 37° C. for 1 hour; after washing with PBS-0.1% Tween20 solution again, the substrate solution o-Phenylenediamine (OPD)-0.1% H$_2$O$_2$ was added for staining about 10-15 minutes, then 0.1M HCl solution was added to quench the reaction. Thereafter, the OD values at 492 nm were read in a multimode reader (PerkinElmer Victor X3).

More than 600 hybridoma cell clones of mice were screened, and more than ten clones with positive anti-CD38 antibody secretion were obtained (the determination criteria of positive clones: the OD value was more than five times higher than that of the negative control sample).

FIG. 2A was the code-names and detecting OD values of various hybridoma cell lines secreting binding positive CD38 antigen screened by ELISA. These positive hybridoma cells were amplified, cultured, and frozen at negative 70° C.

Example 2: Screening and Detecting Hybridoma Cell Culture Supernatant with Positive Anti-CD38 Antibody Secretion by CDC Method In Vitro In the present example, the CDC method in vitro screening and detecting the hybridoma cell culture supernatant with positive anti-CD38 antibody secretion in vitro was summarized as follows:

2.1 Experimental Materials

Cell culture medium: RPMI-1640 Hyclone

Fetal bovine serum (FBS): Gibco, USA

Target cells: human B-lymphoma cell line Daudi (human CD38*, CD20*, B-lymphoma cell lines or other tumor cell lines, purchased from Cell Bank of Typical Culture Preservation Council, Chinese Academy of Sciences)

Source of complement: human serum/young rabbit serum/rabbit complement (healthy) (self-made)

Sample for test: the hybridoma cell culture supernatant with positive anti-CD38 antibody secretion (self-made)

Positive control samples: Daratumumab (humanized anti-CD38 monoclonal antibody) or Rituximab (anti-CD20 Human-Mouse Chimeric Antibody)

Negative control sample: hPV19 monoclonal antibody (humanized anti-VEGF monoclonal antibody)

Cell Viability Assay Kit: CellTiter-Glo® Luminescent Cell Viability Assay Kit (Promega)

96-well cell culture plates: Corning-3610

2.2 Experimental Steps 1) 10 µl sample for test after dilution (the maximum initial concentration of antibody sample was 20-200 g/mL with 5-fold or 3-fold serial dilution. The supernatant of hybridoma cells was directly sampled at 10 µl and loaded) was added into the corresponding wells of 96-well plates;
2) The target cells of the logarithmic growth phase (Daudi cells or other cells with positive CD38 antigen expression) were collected, then washed once with CDC diluent (1% FBS RPMI1640 medium) and counted, the cell viability rate should be more than 90%, and the density of resuspended cells was adjusted to $2.5 \times 10^5$/ml.
3) Target cells were added to 96-well plates (Corning-3610), 80 µl/well, about $2 \times 10^4$ cells/well, then incubated in an incubator at 37° C. for 30 minutes;
4) Diluted human serum or rabbit serum (diluted with CDC diluent at 1:10 or 1:20 firstly) was added at 10 µl/well, then incubated in an incubator at 37° C. for 1 to 2 hours;
5) Before Cell Viability kits were added, the cell culture plates, CellTiter-Glo® Luminescent Cell Viability kits, and 96-well plates were stayed for 30 minutes away from light to balance to room temperature. Then 100 uL prepared reagent was added into each well, stain for 10-15 minutes at room temperature away from light, the RFU (Relative Fluorescence Unit, or Relative Luminescent Unit, RLU) was measured in a multimode reader (PerkinElmer Victor X3).

2.3 CDC Activity Calculation

CDC activity can be directly numerically labeled with RFU or cell lysis rate of CDC can be calculated according to the following formula:

Cell lysis rate (%)=100×(1-(RFU of sample wells)/ ((RFU cells+serum wells))

Cell viability was calculated according to the following formula:

Cell viability (%)=100×((RFU sample wells)/(RFU-cells+serum wells))

2.4 Detecting Results of CDC Activity

Figure 2B:
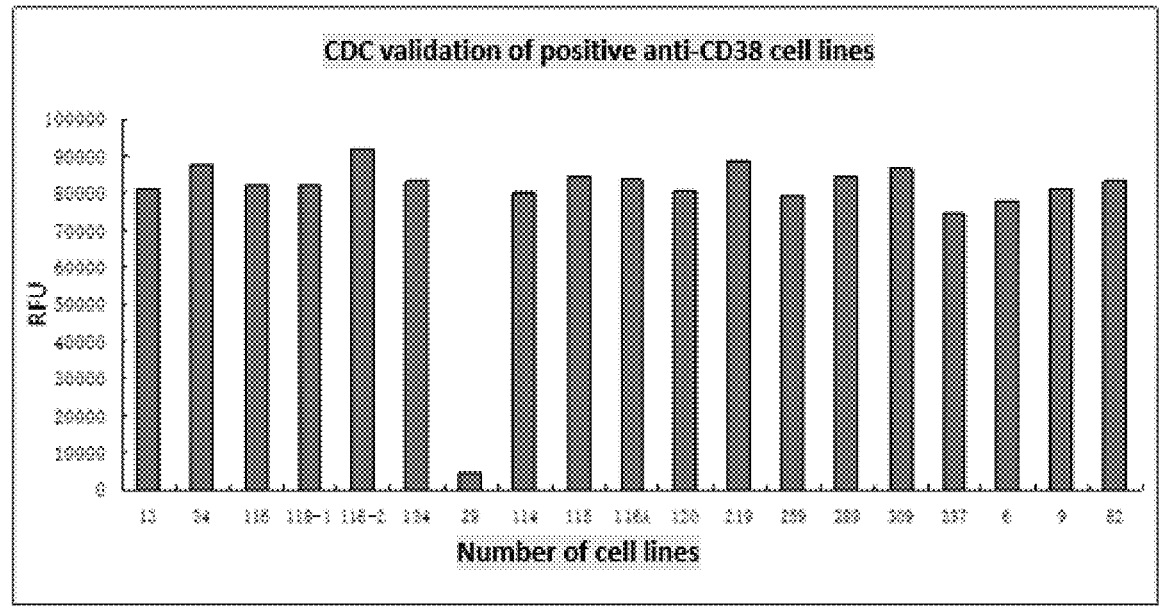
FIG. 2B is a schematic diagram of activity results: validating the supernatant of hybridoma cell lines secreting anti-CD38 antibody screened by ELISA capable of killing Daudi target cells in vitro using CDC method in Example 2 of the present invention; wherein the target cells used are Daudi cells, RFU is an abbreviation of Relative Fluorescence Unit.

FIG. 2B is the activity results of detecting and analyzing the hybridoma cell line supernatant secreting anti-CD38 antibody capable of killing the target cells Daudi in vitro (RFU direct value) by CDC method; wherein the supernatant of a hybridoma cell line code-named m29 showed significant CDC activity (RFU value decreased by more than 95% compared with other samples); however, the supernatant samples of other hybridoma cell lines did not show significant CDC activities (there was no significant decrease in RFU value).

Figure 3A:
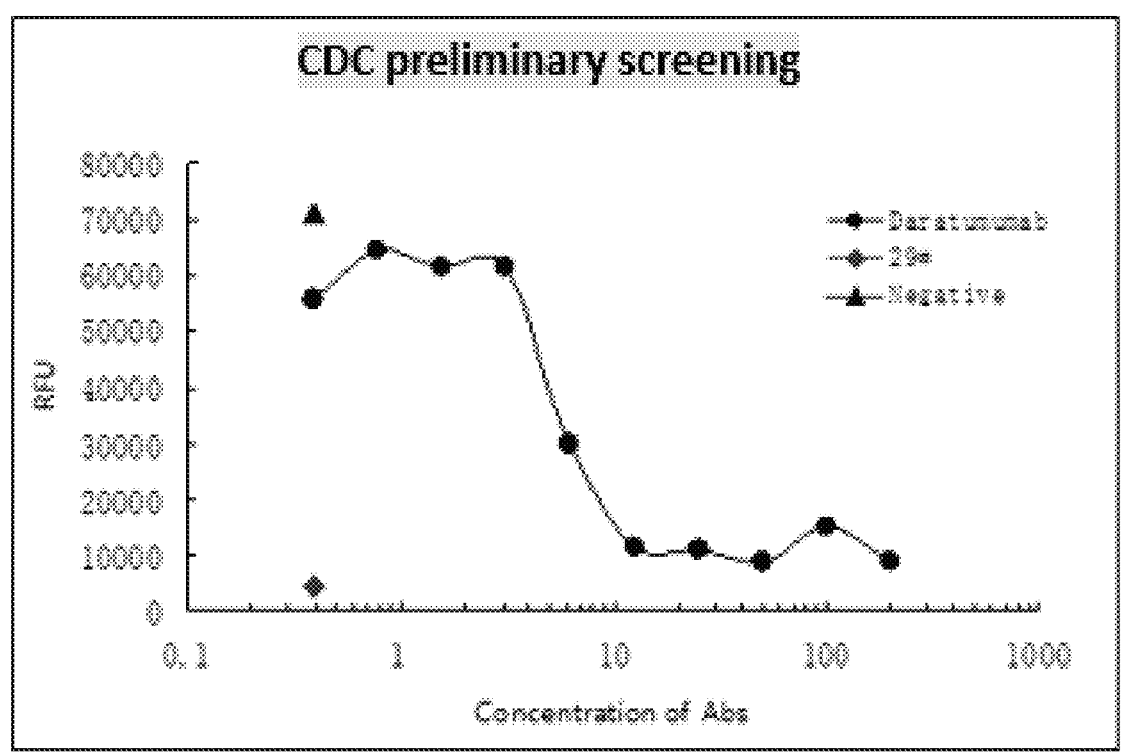
FIG. 3A is a schematic diagram of CDC activity of the supernatant of mouse hybridoma cell line m29 further detected and analyzed by CDC method in Example 3 of the present invention; wherein the target cells used are Daudi, the positive control sample is Daratumumab, and the negative control sample is a mouse SP2/0 myeloma cell line.
Figure 3B:
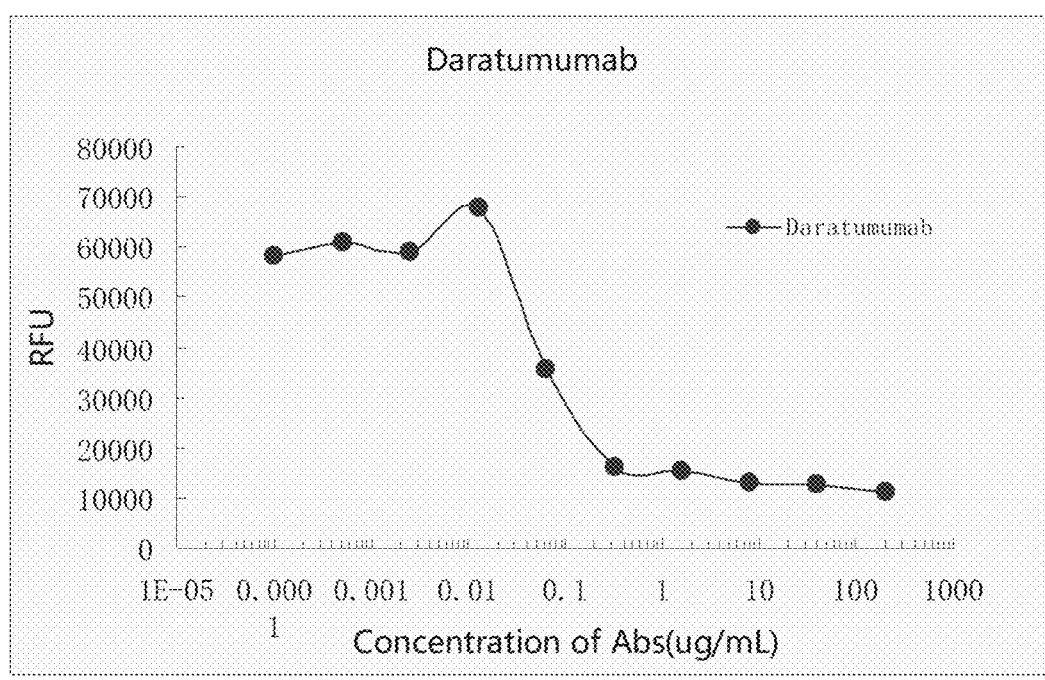
FIG. 3B is a schematic diagram of CDC testing result of the positive control sample Daratumumab in Example 3 of the present invention.

Example 3: Isotype Identification of Murine Monoclonal Antibody m29 and Revalidation of CDC Activity Thereof Murine monoclonal antibody m29 was identified as IgG2b isotype using a commercial mouse monoclonal antibody IgG subclass test card (Beijing Biodragon Immunotech Co., LTD., item No. BF06038). After that, the activity of the supernatant of the hybridoma cell line m29 for killing target cells Daudi was revalidated by CDC in vitro, the results were shown in FIGS. 3A-3C.

Wherein FIG. 3A is the RFU value of the supernatant sample of the hybridoma cell line m29 without dilution directly added into CDC testing plates; the results showed again that the supernatant of a hybridoma cell line m29 showed significant CDC activity (RFU value decreased by more than 95% compared with negative control);

FIG. 3B is the activity results of positive control samples Daratumumab with different solubility for killing target cells Daudi by CDC in vitro; the results showed a significant dosage-response curve.

Figure 3C:
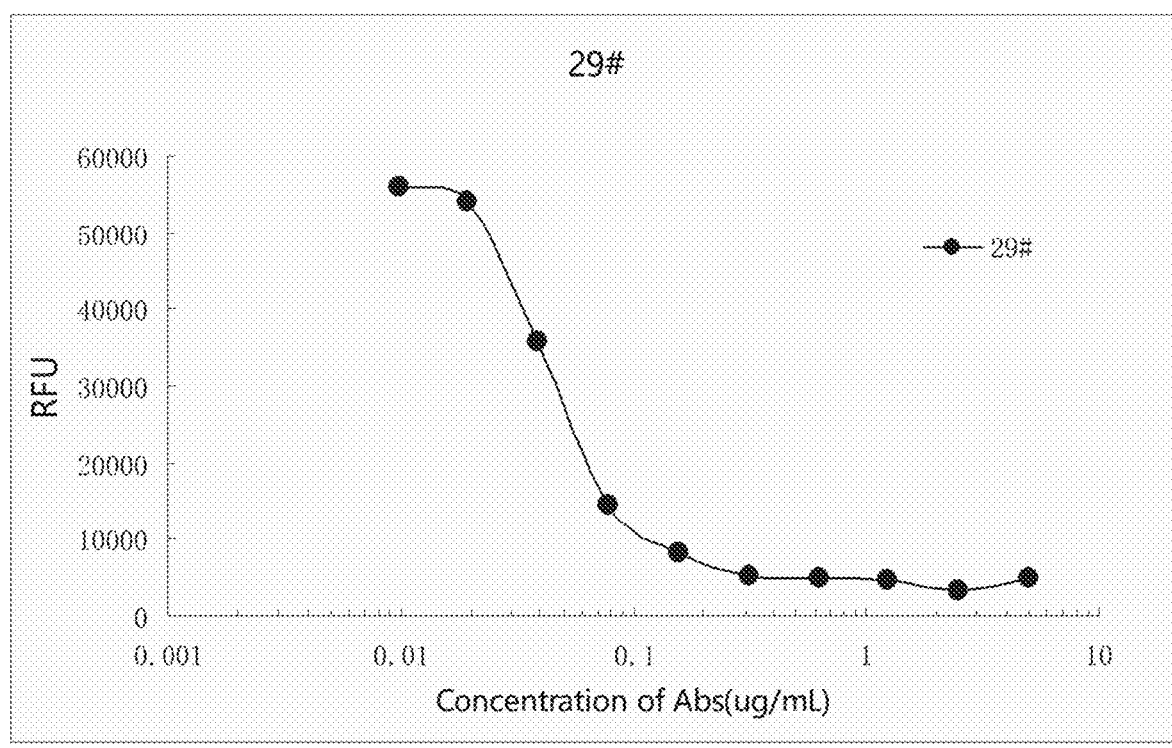
FIG. 3C is a schematic diagram of CDC testing result of the supernatant sample of the mouse hybridoma cell line m29.

FIG. 3C is the activity results of monoclonal antibody samples m29 with different solubility for killing target cells Daudi by CDC in vitro; the results also showed a significant dosage-response curve.

Example 4: Detecting and Analyzing Binding of Murine Monoclonal Antibody m29 to Tumor Cell Lines Expressing Human CD38 Antigen by Flow Cytometer In the present example, the supernatant sample of hybridoma cell line m29 or a non-related murine hybridoma mAB21 sample (mouse anti-human PD-1 monoclonal antibody) used as a primary antibody, FITC-Goat anti-Mouse IgG was used as a second antibody, the binding of the sample to the human tumor cell lines with positive CD38 antigen expression was detected and analyzed by flow cytometer.

For this purpose, the tumor cell lines with positive CD38 antigen (B-lymphoma cell line Daudi, myeloma cell line RPMI-8226, and T-lymphoma cell line MOLT-4, purchased from Cell Center of Shanghai Institute of Life Sciences, Chinese Academy of Sciences) respectively were mixed with the supernatant sample of the hybridoma cell line m29 or a non-related murine hybridoma mAB21 sample (mouse anti-human PD-1 monoclonal antibody) to incubate at 4° C. for 1 hour; after washing with PBS-0.1% FCS solution, FITC-Goat anti-Mouse IgG (diluted at 1:200, Sigma) was added and incubated at 4° C. for 1 hour; after washing with PBS-0.1% FCS solution again, the sample was loaded into Accuri C6 Plus Flow Cytometer (Becton Dickinson, USA; Mountain View, CA, USA).

Figure 4A:
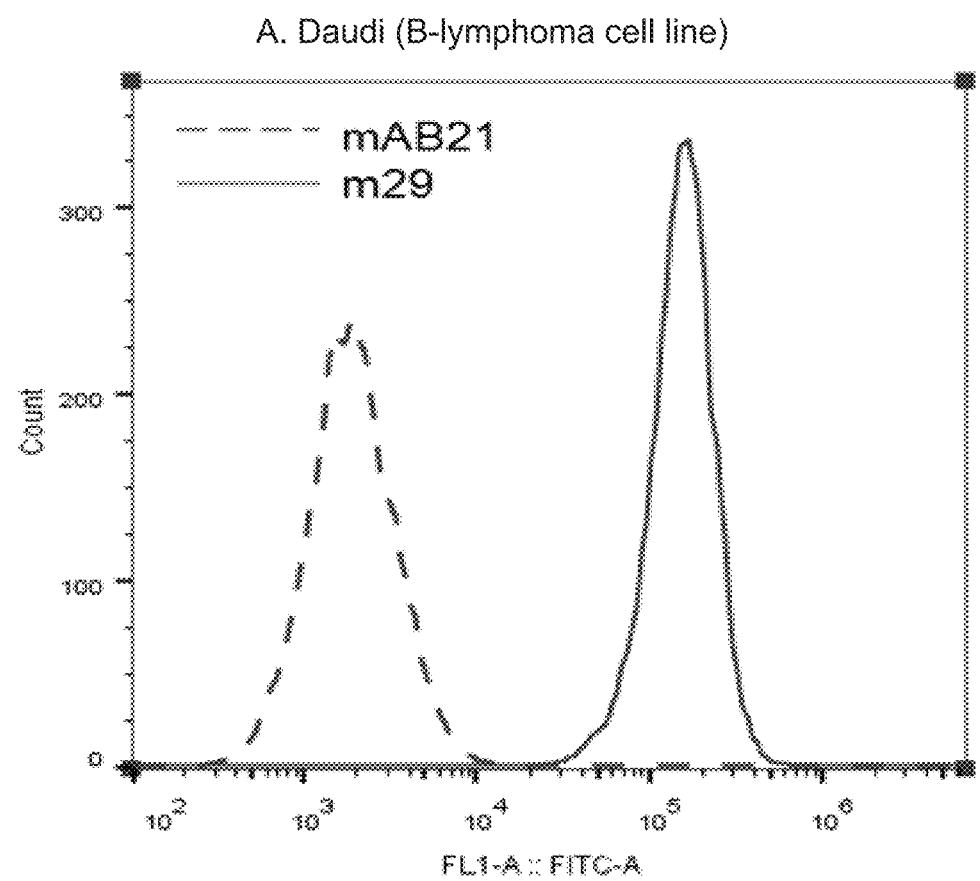
Figure 4B:
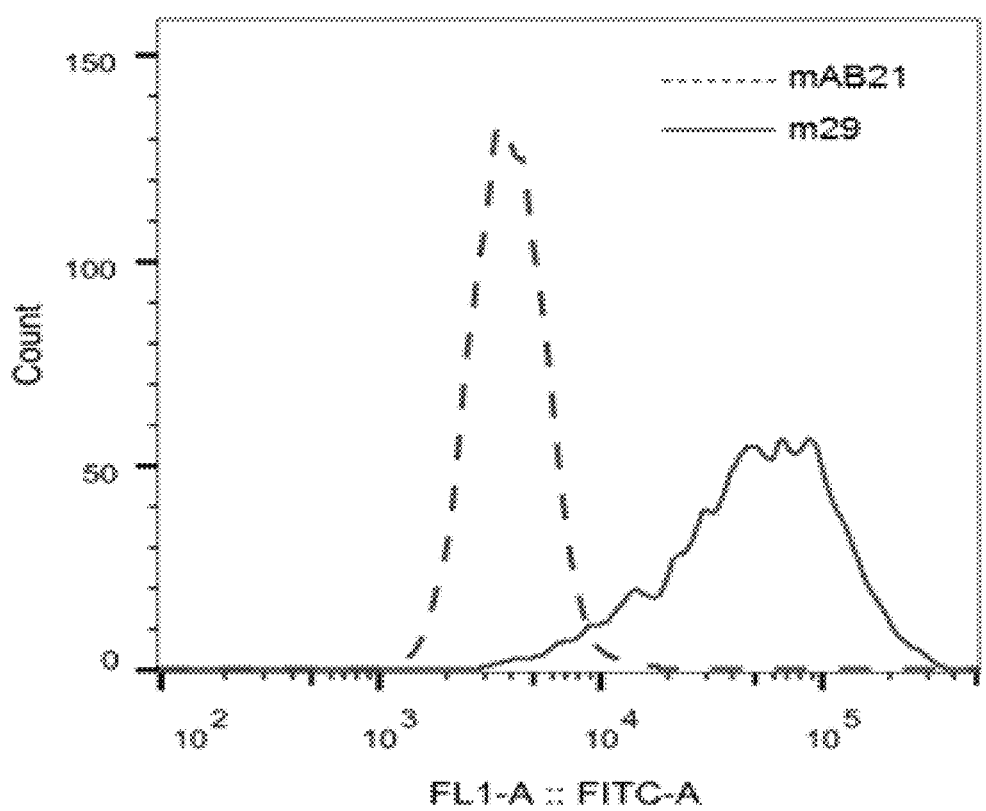
Figure 4C:
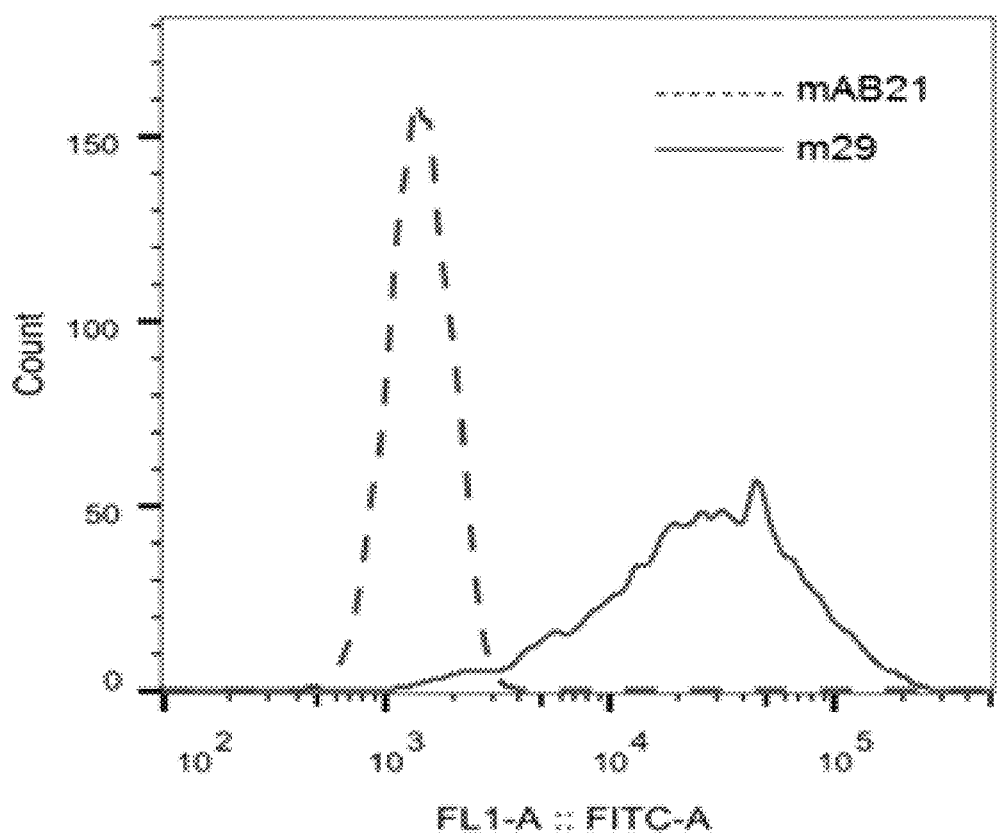

FIGS. 4A-4C are the representative results by flow cytometer. As shown in FIGS. 4A-4C, compared with the non-related murine hybridoma mAB21 sample (mouse anti-human PD-1 monoclonal antibody), the supernatant sample of the hybridoma cell line m29 can significantly bind to the tumor cell lines with positive CD38 antigen, such as human B-lymphoma cell line Daudi (FIG. 4A), myeloma cell line RPMI-8226 (FIG. 4B) and T-lymphoma cell line MOLT-4 (FIG. 4C).

Example 5: Detecting and Analyzing Binding of Supernatant Samples of m29 Hybridoma Cell Line and Daratumumab to CHO Cells Stably Transfected with Human CD38 Gene and Expressed the Gene (CHO-hCD38) by Flow Cytometer 5.1 Construction of CHO Cell Lines (CHO-hCD38) Stably Expressing Human CD38 Gene According to human CD38 gene sequences published in Genbank (Gene ID: 952), the cDNA fragments of coding CD38 were delegated to Suzhou Genewiz Biological Technology Co. LTD to synthesize, then cloned them into the cell expression plasmid pQY-DHFR (self-made), transferred into E. coli, the recombinant expressing plasmid pQY-DHFR-hCD38 was identified by restriction endonuclease digestion. After that, the recombinant plasmid pQY-DHFR-hCD38 and Fugen-6 liposome (Roche) were mixed and co-transfected into CHO-dhfr cell, then CHO cell lines stably expressing human CD38 (CHO-hCD38) gene were successfully obtained by screening in IMDM culture medium containing FBS.

5.2 Detecting and Analyzing Binding of Supernatant Samples of Murine m29 Hybridoma Cell Line and Daratumumab to CHO Cells Stably Expressing Human CD38 Gene (CHO-hCD38) by Flow Cytometer In the present example, the supernatant sample of the murine m29 hybridoma cell line or positive sample Daratumumab used as a primary antibody, FITC-Goat anti-Mouse IgG or FITC-Goat anti-human IgG was used as a second antibody, the binding of the sample to human CD38 cell lines stably expressing human CD38 antigen was detected and analyzed by flow cytometer.

For this purpose, CHO-hCD38 cells respectively were mixed with the supernatant sample of the murine m29 hybridoma cell line, positive sample Daratumumab, the non-related murine hybridoma mAB21 sample (mouse anti-human PD-1 monoclonal antibody), or the humanized monoclonal antibody sample hAB21 to incubate at 4° C. for 1 hour; after washing with PBS-0.1% FCS solution, FITC-Goat anti-Mouse IgG (diluted at 1:200, Sigma) was added (FTTC-Goat anti-Human IgG (diluted at 1:200, Sigma) was added if corresponding to Daratumumab sample), and incubated at 4° C. for 1 hour; after washing with PBS-0.1% FCS solution again, the samples were loaded into Accuri C6 Plus Flow Cytometer (Becton Dickinson, USA; Mountain View, CA, USA).

Figure 5A:
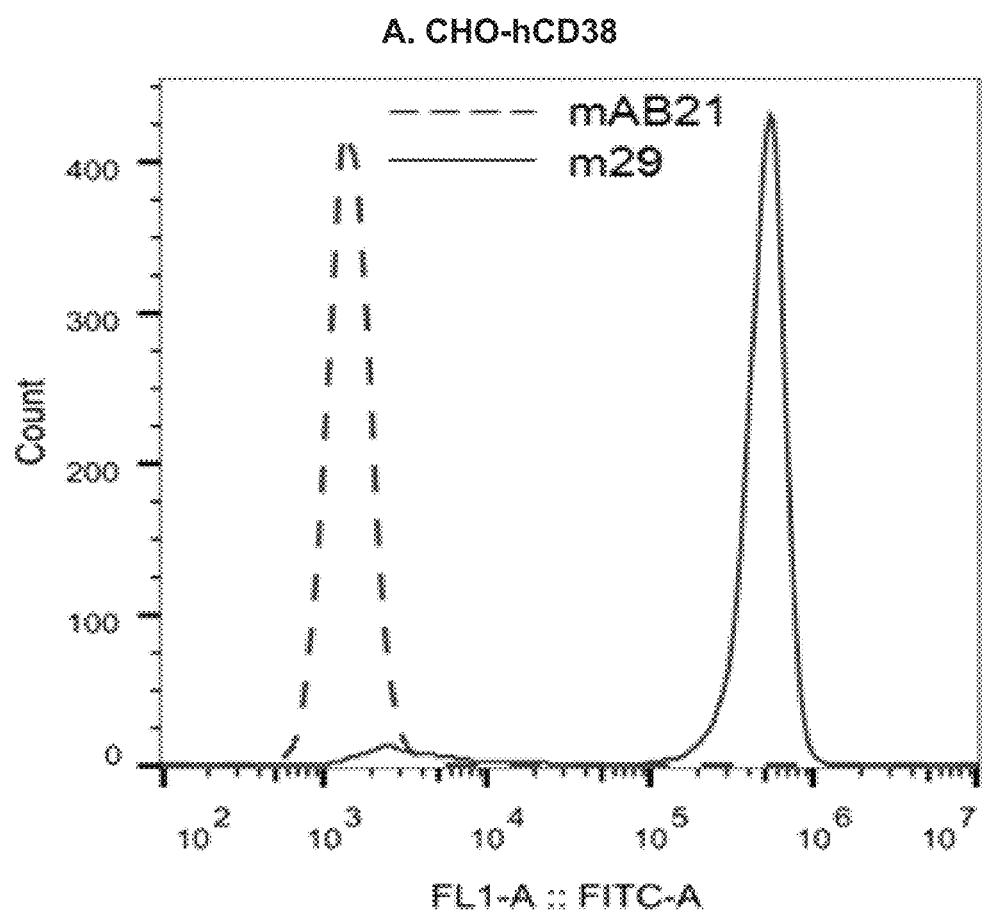
Figure 5B:
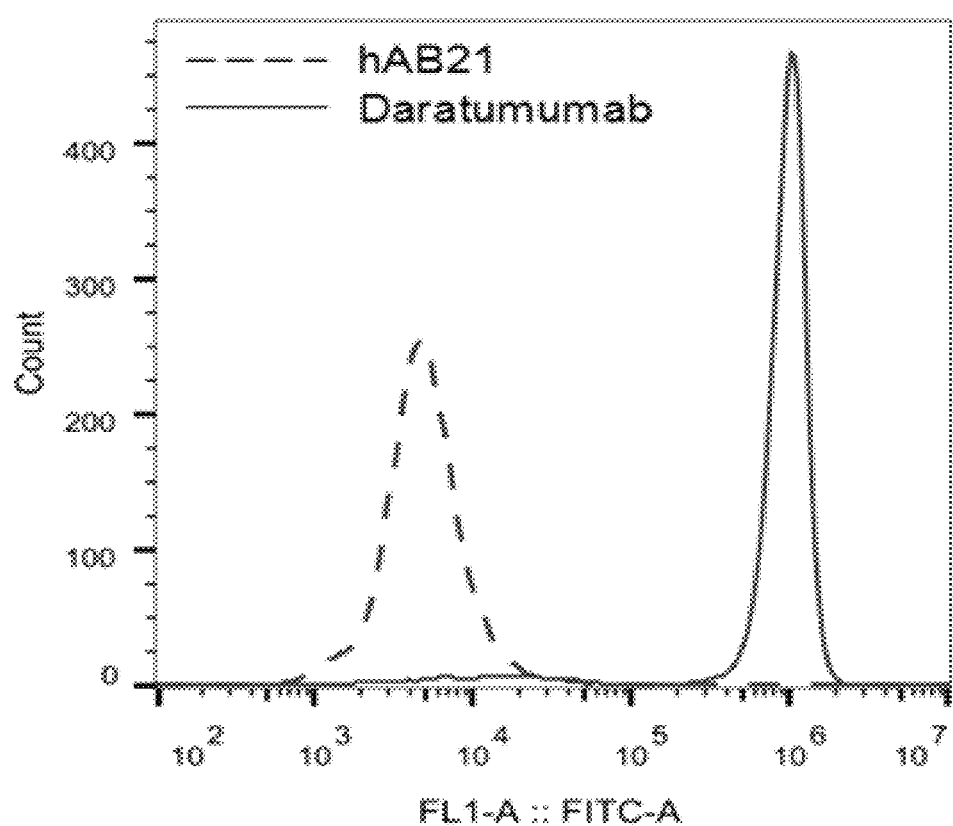

FIGS. 5A-5B are the representative results detecting CHO-hCD38 by flow cytometer. As shown in FIGS. 5A-5B, the supernatant sample of the murine m29 hybridoma cell lines (FIG. 5A) and Daratumumab sample (FIG. 5B) can significantly bind to CHO-hCD38 cells, compared with the negative control sample the non-related murine hybridoma mAB21 or hAB21; wherein the binding intensity of monoclonal antibody sample m29 to CHO-hCD38 cell was no less than Daratumumab.

Example 6: Isolation and Purification of Murine Monoclonal Antibody m29 and Detecting Competitive Binding of Monoclonal Antibody m29 and Daratumumab to CD38

6.1: Isolation and Purification of Murine Monoclonal Antibody m29

The m29 hybridoma cells were amplified and adapted to culture in serum-free medium (KD-Hybri, Zhuhai Kairui Biotech Co Ltd.). A certain amount of serum-free cell culture supernatant was collected, after centrifugation and filtration with a 0.45 μm filtration membrane, then loaded to a Protein-G affinity chromatography column (Protein G-Sepharose Fast Flow, GE, USA). After rinsing by 1×PBS and eluting with buffer solution (0.05 m sodium acetate, pH=3.2), the antibody m29 was obtained. Thereafter, the buffer was changed to glycine-Tris (pH=6.0) by centrifugation with ultrafiltration device (Millipore UFC903096, 30kD), and the purified m29 antibody was stored at 4° C. after quantitative labeling.

6.2 Detecting and Analyzing Competitive Binding of Murine Monoclonal Antibody m29 and Daratumumab to CD38 by Competitive ELISA In Vitro The basic principle and process of the competitive ELISA were as follows: m29 monoclonal antibody samples or Daratumumab with different solubility were mixed with biotin-labeled m29 monoclonal antibody sample (biotin-m29) or biotin-labeled Daratumumab (biotin-Daratumumab), then the mixture was transferred to 96-well plates pre-coated with CD38-His recombinant protein, incubated and eluted, enzyme-labeled Avidin (HRP-Avidin) was added; incubated and eluted again, the substrate was added for staining and detecting the OD values.

In the present example, the detailed steps of the competitive ELISA method were as follows:
1) the 96-well cell culture plates were coated (coating concentration: 2 μg/ml, 50 μl/well) with the recombinant human CD38 extracellular membrane protein (Sino Biological Inc.), incubated overnight at 4° C.
2) after washing with PBS solution and 5% milk (diluted in PBS-0.1% Tween20 solution), the plates were sealed at room temperature, followed by the separate addition of anti-CD38 monoclonal antibodies with different solubility (m29 or Daratumumab) or the non-related antibody (anti-VEGF monoclonal antibody hPV19) and biotin-labeled Daratumumab (biotin-Daratumumab, diluted at 1:1000) or biotin-labeled m29 monoclonal antibody (biotin-m29, diluted at 1:1000) with fixed concentration, incubated at 37° C. for 1.5 h;
3) After eluting with PBS-T solution, the HRP-Avidin (diluted at 1:500) was added and incubated at 37° C. for 1 hour;
4) After eluting with PBS-T solution again, the chromogenic substrate solution OPD-3% $H_2O_2$ was added for staining for 10 minutes at room temperature.
5) 1M HCl solution was added to quench the reaction, then the absorption values of various wells at 492 nm wavelength were read in an enzyme-linked immunometric meter.

Figure 6A:
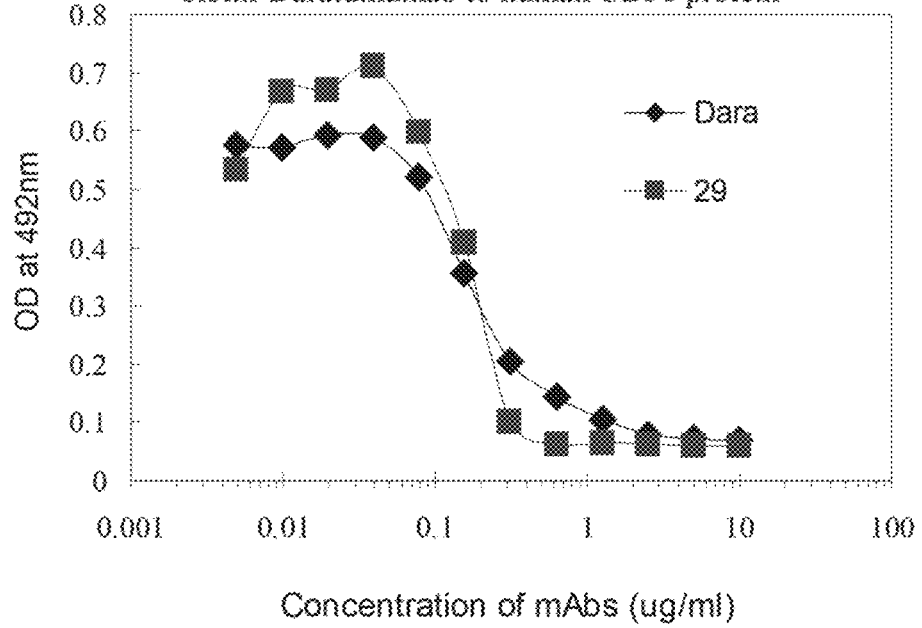
Figure 6B:
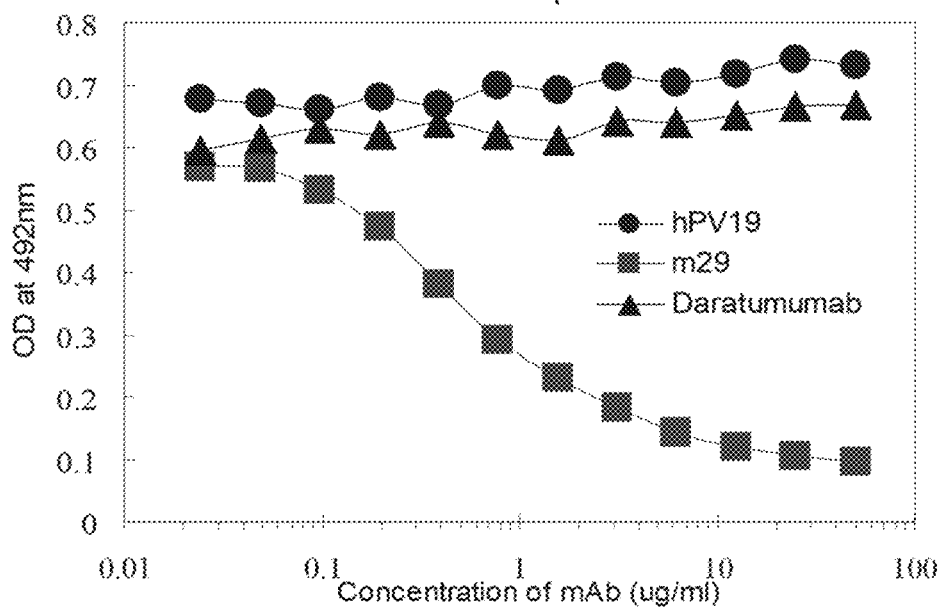

FIGS. 6A-6B are the schematic diagrams of the representative results of the competitive ELISA; wherein FIG. 6A is the results of the competitive binding of m29 monoclonal antibody and Daratumumab to biotin-Daratumumab in vitro; as shown in FIG. 6A, m29 monoclonal antibodies or Daratumumab at different concentrations and biotin-Daratumumab samples at fixed concentration were added, the OD value of chromogenic reaction in each well was inversely proportional to the amount of labeled-antibodies: namely the higher the amount of m29 monoclonal antibody or Daratumumab was added, the lower the OD value of chromogenic reaction was. The results also illustrated that, as the same with Daratumumab, m29 monoclonal antibody could competitively bind to CD38 with biotin-Daratumumab in vitro; furthermore, m29 monoclonal antibody also achieved almost the same competitive binding effect to CD38 with Daratumumab.

FIG. 6B is the competitive binding results of m29 monoclonal antibody, Daratumuma, and biotin-m29 monoclonal antibody to CD38 in vitro; as shown in FIG. 6B, m29 monoclonal antibody at different concentration and biotin-m29 samples at fixed concentration were added, the OD value of chromogenic reaction in each well was inversely proportional to the amount of unlabeled m29 antibodies: namely the higher the amount of m29 monoclonal antibody was added, the lower the OD value of chromogenic reaction was; in contrast, the amount of Daratumumab or the amount the non-related monoclonal antibody sample hPV19 had little influence on the OD value of each well. The results also illustrated that Daratumumab did not competitively bind to CD38 with m29 monoclonal antibody in vitro.

In summary, the competitive ELISA results showed that the binding epitope of m29 monoclonal antibody to human CD38 protein is different from Daratumumab, and m29 monoclonal antibody can competitively block the binding of Daratumumab to human CD38 protein; in contrast, Daratumuma cannot block the binding of m29 monoclonal antibody to human CD38 protein.

Example 7: Cloning of the Gene Coding Variable Regions of Murine Monoclonal Antibody m29

Herein, the total RNA was extracted from the mouse m29 hybridoma cells, and used as a template; together with the degenerate primers, to clone and amplify the cDNA gene fragments of m29 antibody heavy chain variable region and light chain variable region respectively by reverse transcription-polymerase chain reaction (RT-PCR) method (Wang Y et al: Degenerated primer design to amplify the heavy chain variable region from immunoglobulin cDNA. BMC Bioinformatics. 2006; 7 Suppl (4): S9).

Wherein the cDNA gene cloning steps were as follows:

Step 1: The total RNA was extracted from the mouse m29 hybridoma cells with a kit (Beyotime Biotechnology, Haimen, Jiangsu)

Step 2: cDNA template was obtained in Eppendorf tube by RT-PCR method

Wherein, the sequence of the RT-PCR primer mKaRT for m29 antibody light chain variable region was TGT CGT TCA CTG CCA TCA AT (SEQ ID NO: 18);

The sequence of the RT-PCR primer mGaRT for m29 antibody heavy chain variable region was GCA AGG CTT ACA ACC ACA ATC (SEQ ID NO: 19);

RT-PCR reaction system was as follows:

| | |
|---|---|
| Primers | 2 µl |
| RNA template | 30 µl |
| Incubated at 72° C. for 10 minutes, then stayed on the ice for 2 minutes; Followed by: | |
| 5 × Rf-PCR reaction buffer solution | 10 µl |
| dNTPs | 5 µl |
| PrimeScript reverse transcription-polymerase | 1.5 µl |
| Distilled water | 1.5 µl |
| Total volume | 50 µl |

Incubated at 72° C. for 10 minutes, then stayed on the ice for 2 minutes;

Followed by:

Reacted at 42° C. for 1 hour, then increased the temperature to 75° C., after 15 minutes of inactivation, the cDNA was obtained and stored at −20° C. for later use.

Step 3: PCR cloning and amplification of m29 antibody light chain variable region gene and heavy chain variable region gene The following pair of primers used in cloning and amplification of m29 antibody light chain variable region gene by degenerate primers PCR method were as follows:

```
Forward primer mIgLF1:
                                      (SEQ ID NO: 20)
GACATTGTGATGWCM CA;

Reverse primer mIgLCR440:
                                      (SEQ ID NO: 21)
CTGAGGCACCTCCAGATGTT.
``` wherein W=A or T, M=A or C₀

The following pair of primers used in cloning and amplification of m29 antibody heavy chain variable region gene by degenerate primers PCR method were as follows:

```
Forward primer mIgHset1:
                                      (SEQ ID NO: 22)
CARCTGCARCARYCT;
```

Wherein R=A or G, Y=C or T₀

```
Reverse primer mIgHCR135:
                                      (SEQ ID NO: 23)
GTGCTGGAGGGGACAGTCACT.
```

DNA products amplified by PCR were analyzed by electrophoresis in 1% agarose gel. When electrophoresis is over, the separated bands were cut and sequenced to obtain the nucleotide sequences of the DNA of antibody light and heavy chain variable region. The nucleotide sequence of DNA of the light chain variable region was set forth in SEQ ID NO: 1. The amino acid sequence of DNA of the light chain variable region inferred from the DNA nucleotide sequence was set forth in SEQ ID NO: 2. The amino acid sequences of complementarity-determining regions (CDR) CDR1, CDR2, and CDR3 of the light chain antigen were set forth in SEQ ID NO: 3, SEQ ID NO: 4, and SEQ ID NO: 5, respectively.

The nucleotide sequence of DNA of the heavy chain variable region was set forth in SEQ ID NO: 6, and the amino acid sequence of DNA of the heavy chain variable region inferred from the DNA nucleotide sequence was set forth in SEQ ID NO: 7. The amino acid sequences of complementarity-determining regions (CDR) CDR1, CDR2, and CDR3 of the heavy chain antigen were set forth in SEQ ID NO: 8, SEQ ID NO: 9 and SEQ ID NO: 10, respectively.

FIG. 7A is amino acid sequences comparison analysis result of coding the light chain variable regions of m29 antibody and Daratumumab; wherein different amino acid sequences of the light chain variable regions between m29 antibody and Daratumumab were marked in "X", CDR1, CDR2, and CDR3 of all kinds of antibodies light chain variable regions were marked in Box. The comparison analysis result showed that the light chain variable regions of m29 and its CDR sequences were obviously different from Daratumumab.

FIG. 7B is amino acid sequences comparison analysis result of coding the heavy chain variable regions of m29 antibody and Daratumumab; wherein different amino acid sequences of the heavy chain variable regions between m29 antibody and Daratumumab were marked in "X", CDR1, CDR2, and CDR3 of all kinds of antibodies heavy chain variable regions were marked in Box. The comparison analysis result showed that the heavy chain variable region of m29 and its CDR sequences were obviously different from Daratumumab.

Example 8: Construction of Human-Mouse Chimeric Antibody (ch29G) Derived from Murine Antibody m29 m29 antibody light and heavy chain variable region genes obtained by cloning and amplification in Example 7 were fused respectively with a human kappa light chain constant region (C-domain) and a human IgG1 heavy chain constant region fragment gene to obtain the human-mouse chimeric light chain gene (ch29L) and the human-mouse chimeric heavy chain gene (ch29H). After that, the light and heavy chain chimeric genes were successively cloned into the expression plasmid pQY-DHFR-Hex, then transferred into E. Coli to amplify, and separated to obtain lots of expression plasmids containing the human-mouse chimeric antibody gene.

The expression plasmids containing the human-mouse chimeric antibody gene and X-tremeGENE HP DNA Transfection Reagent liposome (Roche) were mixed and transfected into CHO-dhfr cells. After 2 to 3 days of cells transfection, the culture supernatant was collected and transferred to the 96-well plates coated with human CD38-his protein, HRP-Goat anti-Human IgG was added as a second tested antibody (Purchased from Shanghai Xitang Biology company), to detect the binding of the chimeric antibody (ch29G) in the supernatant to human CD38-his protein by ELISA.

The ELISA representative results were shown in the following Table 3:

TABLE 3

Detecting binding, of CHO cell culture supernatant transiently transfected with chimeric antibody(ch29G) gene to human CD38-his protein by ELISA

| | Supernatant Dilution Times | | | | | | |
|---|---|---|---|---|---|---|---|
| 1 | 2 | 4 | 8 | 16 | 37 | 64 | 128 |
| OD492 values 0.953 | 0.865 | 0.698 | 0.518 | 0.321 | 0.230 | 0.113 | 0.077 |

The results of Table 3 demonstrated that the CHO cell culture supernatant transfected with the plasmid expressing human-mouse chimeric antibody gene ch29G can specifically bind to human CD38 protein.

After that, the above-transfected cells were passaged to the culture dish, and the conditioned medium was added to screen the stable expression cell lines. After 2 to 3 weeks of culturing, the well-grown cell clones were selected and moved to 96-well plates. After 2 to 3 days, the supernatant was collected to detect the expression level of protein in the supernatant by ELISA. Finally, the CHO cell line with high expression of ch29 antibody protein was screened out. The cell line was domesticated in serum-free medium (CHOM-B01, Shanghai Baian Medical Investment Co., LTD.), after successful domestication, the supernatant was amplified and collected. After centrifugation and filtration with a 0.45 μm filter membrane, the supernatant was loaded to a Protein-A chromatography affinity column (Protein-A Sepharose Fast Flow, GE, USA), followed by isolation and purification, changed to glycine-Tris (pH=7.0) to obtain the human-mouse chimeric antibody (ch29G, or ch29 for short) with a purity of over 99%.

Example 9: Detecting and Comparing Binding of Murine Monoclonal Antibody m29, Human-Mouse Chimeric Antibody Ch29G, and Daratumumab to Human Tumor Cell Lines Expressing CD38 Antigen by Flow Cytometer In the present example, purified murine m29 monoclonal antibody, human-mouse chimeric antibody ch29G, and Daratumumab or the non-related hAB21 monoclonal antibody (a humanized anti-PD-1 monoclonal antibody) was used as a primary antibody, FITC-Goat anti-Mouse IgG or FITC-Goat anti-human IgG was used as a second antibody, the binding of samples to tumor cell lines with positive CD38 antigen expression was detected by flow cytometer method as described in Example 4.

For this purpose, the human tumor cell lines that are known to express CD38 antigen ((human Burkitt B-lymphoma cell line Raji, Human myeloma cell line RPMI-8226, human T-lymphoma cell line MOLT-4, and human T-lymphoma cell line Jurkat, all purchased from Cell Center of Shanghai Institute of Life Sciences, Chinese Academy of Sciences) respectively were incubated with murine m29 monoclonal antibody, human-mouse chimeric antibody ch29G, Daratumumab or non-related hAB21 monoclonal antibody at 4° C. for 1 hour, rinsed with PBS-0.1% FCS solution, then the FTTC-Goat anti-Mouse IgG (diluted at 1:200; Sigma, USA) or FTTC-Goat anti-human IgG (diluted at 1:200; Sigma, USA) was added and incubated at 4° C. for 1 hour; after rinsing with PBS-0.1% FCS solution again, the samples were loaded to BD Accuri C6Plus Flow Cytometer (Becton Dickinson, USA; Mountain View, CA) for detecting.

FIGS. 8A-8D are the representative results by flow cytometer; wherein

Figure 8A:
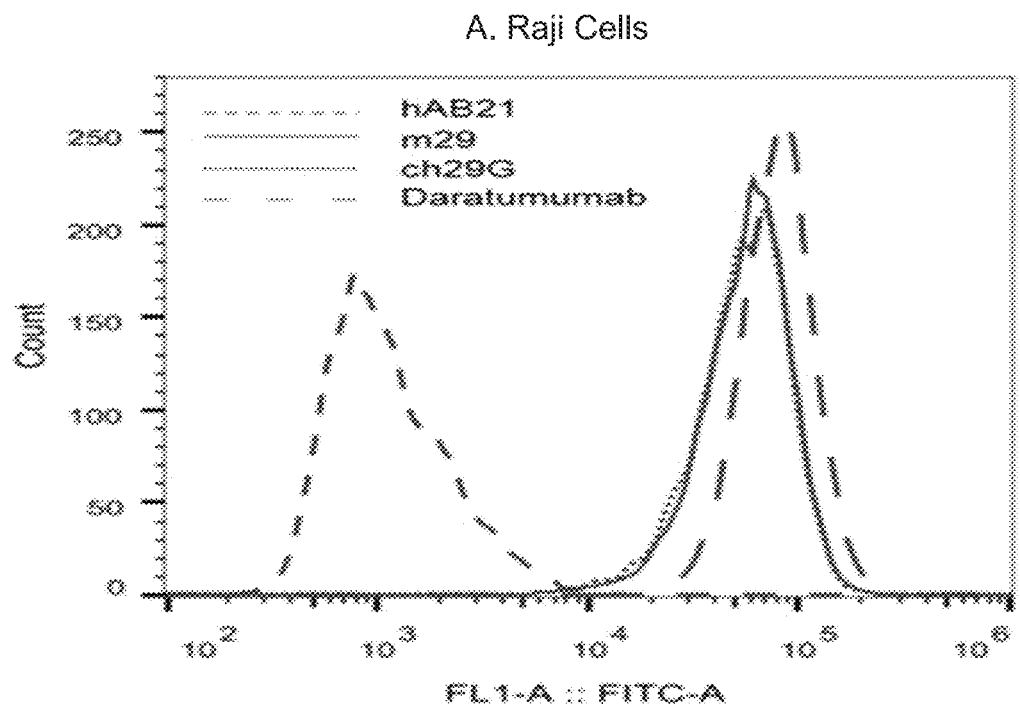

FIG. 8A is the detecting result of human Burkitt B-lymphoma cell line Raji: compared with non-related hAB21 monoclonal antibody, mouse m29 monoclonal antibody, human-mouse chimeric antibody ch29G and Daratumumab all can significantly bind to human Burkitt B-lymphoma cell line; wherein the positive ratio of cell binding and signal intensity of murine m29 monoclonal antibody and human-mouse chimeric antibody ch29G to Raji cells were almost the same with Daratumumab sample.

Figure 8B:
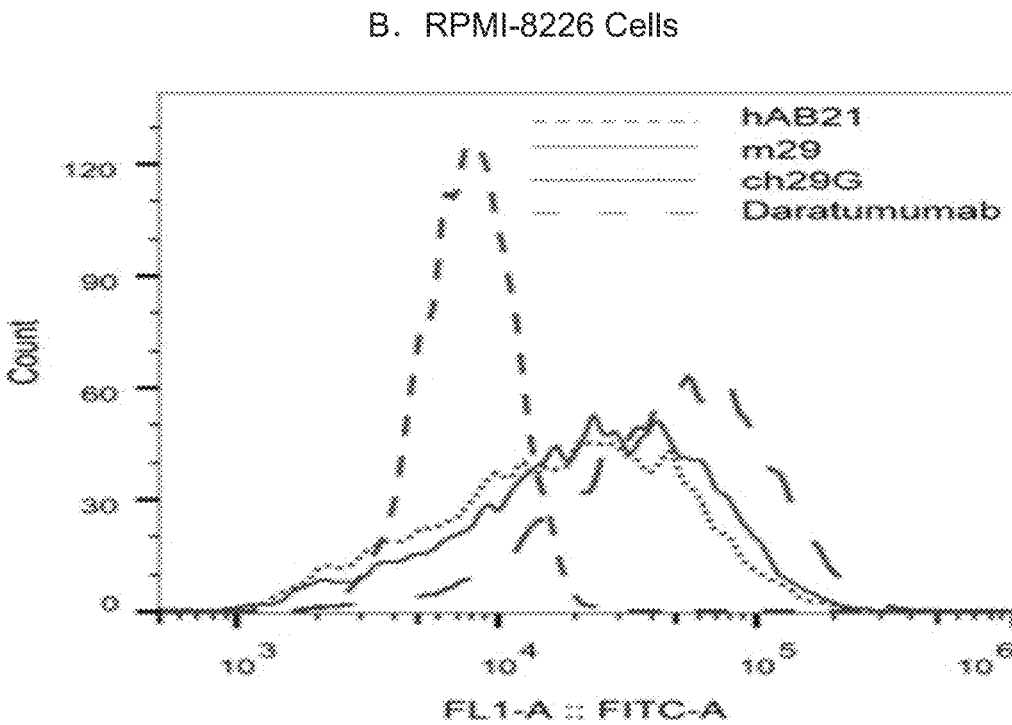

FIG. 8B is the detecting results of Human myeloma cell line RPMI-8226: compared with non-related hAB21 monoclonal antibody, mouse m29 monoclonal antibody, human-mouse chimeric antibody ch29G and Daratumumab all can significantly bind to human Burkitt B-lymphoma cell line; wherein the positive ratio of cell binding and signal intensity of murine m29 monoclonal antibody and human-mouse chimeric antibody ch29G to RPMI-8226 cell were also almost the same with Daratumumab sample.

Figure 8C:
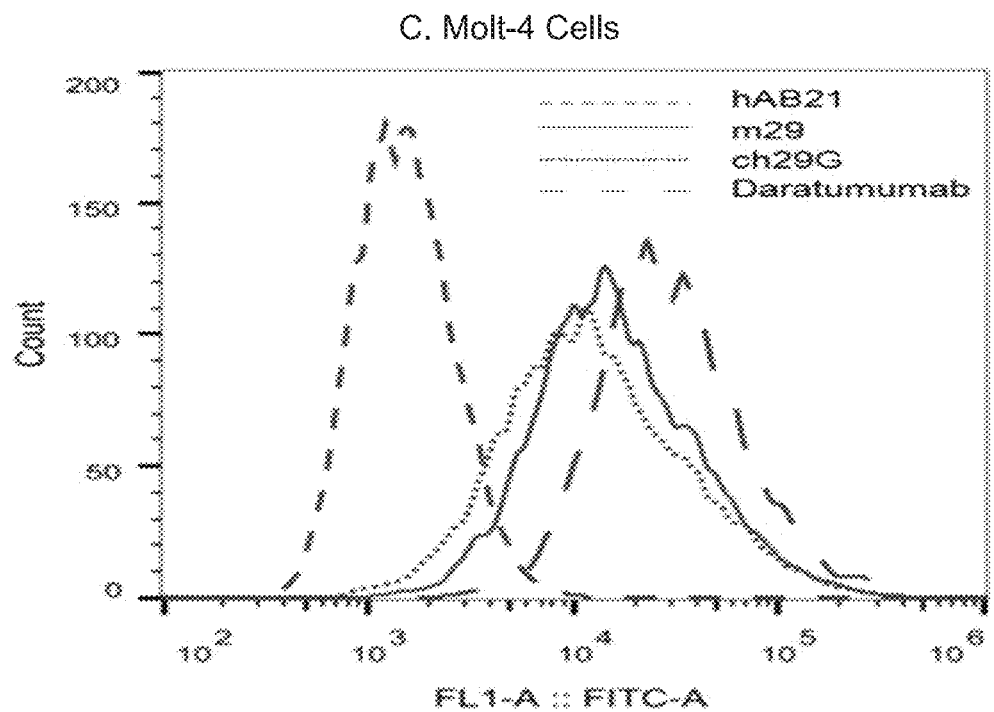

FIG. 8C is the detecting results of human T-lymphoma cell line MOLT-4: the positive ratio of cell binding and signal intensity of murine m29 monoclonal antibody and human-mouse chimeric antibody ch29G to MOLT-4 cell were slightly lower than Daratumumab.

Figure 8D:
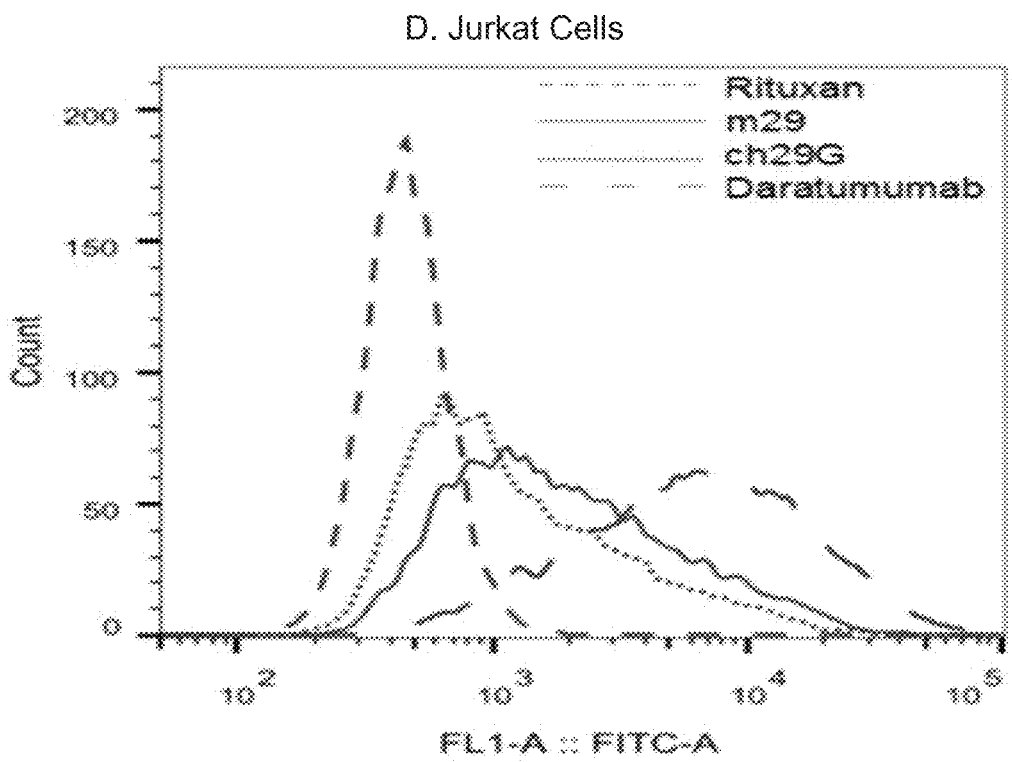

FIG. 8D is the detecting results of human T-lymphoma cell line Jurkat: the positive ratio of cell binding and signal intensity of murine m29 monoclonal antibody and human-mouse chimeric antibody ch29G to Jurkat cell were lower than Daratumumab.

Example 10: Analyzing and Comparing CDC Activities of Murine Monoclonal Antibody m29, Human-Mouse Chimeric Antibody Ch29G, and Daratumumab In Vitro CDC activities in vitro of murine monoclonal antibody m29, human-mouse chimeric antibody ch29G, and Daratumumab were analyzed and compared using the same CDC assay as described in Example 2. In the present example, the target cells used were classical Daudi cells; the complement was 10% rabbit serum (self-made).

Figure 9:
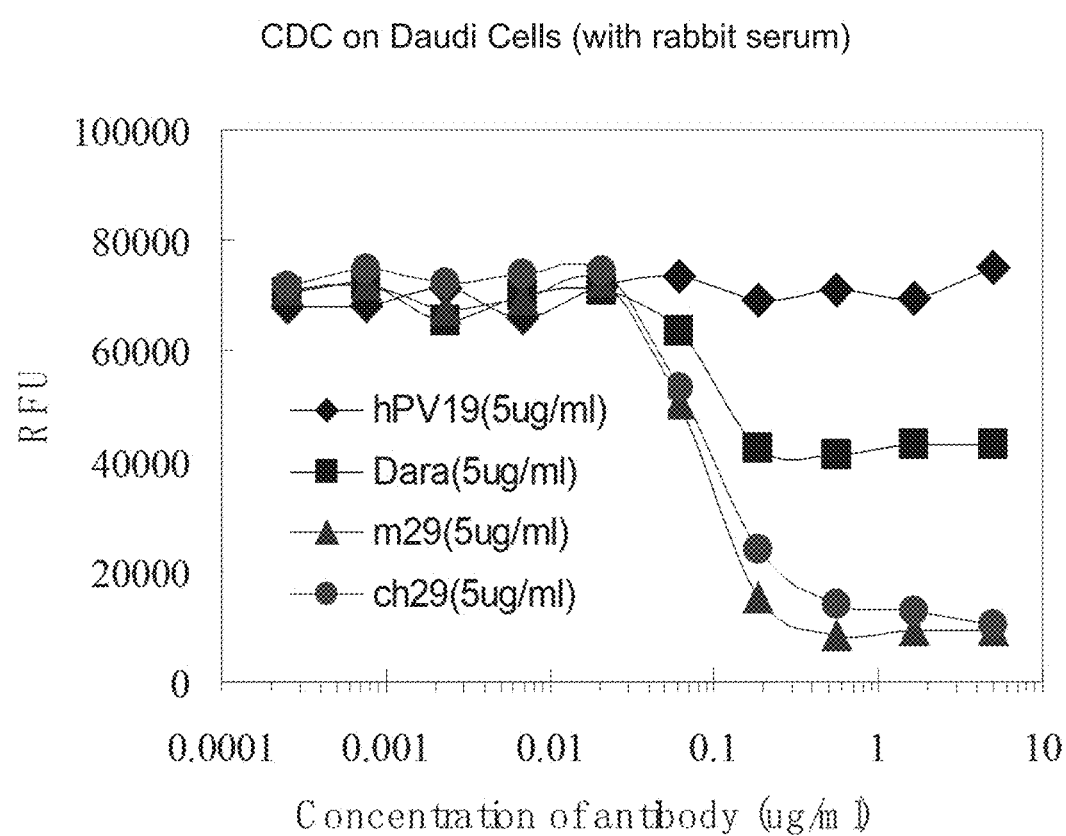
FIG. 9 is a CDC activity diagram of detecting and analyzing the mouse monoclonal antibody m29 sample, the human-mouse chimeric antibody ch29G sample, and the control sample Daratumumab, wherein the target cell used is human B-lymphoma cell line Daudi, the source of complement is rabbit serum, and negative control sample is a non-related humanized hPV19 Mab (anti-VEGF Mab).

FIG. 9 is the CDC activity results. The results showed that CDC activities of murine monoclonal antibody m29 and human-mouse chimeric antibody ch29G were all stronger than Daratumumab. Their maximum CDC activity values were more than 95%, EC50 values were around 30 ng/ml; in contrast, the maximum CDC activity value of Daratumumab was only around 55%, EC50 value was 100 ng/ml.

Example 11: Detecting Binding of Murine Monoclonal Antibody m29, Human-Mouse Chimeric Antibody ch29G, and Daratumumab to CD38 with Point Mutation by Flow Cytometer 11.1 Construction of CHO Cell Lines Stably Expressing Human CD38 Gene with Point Mutation (CHO/hCD38-$S_{274F}$)

In order to mutate serine (S) at C-terminal 274 in human CD38 into phenylalanine (F), the human CD38 cDNA synthesized in Example 5.1 was used as a template to design primers for PCR amplification:

```
Forward Primer huCD38F-HindIII-2:
                                   (SEQ ID NO: 15)
TTGTAAGCTTGCCGCCACCATGGCTAACTGCGAGTTCTCC;

Reverse primer huCD38-S274F-R1
                                   (SEQ ID NO: 16)
CTTATCGGGCCTATAGATATTTTTGCAGAAGAACTGGATGTTCCGCTTGC

TGATGATGC
```

The obtained DNA products were performed electrophoresis to separate the target DNA bands in 1.5% Agarose gel. Then the recycled DNA fragments were used as templates, and the following primers were used to conduct the second round of PCR to achieve the complete hCD38-$S_{274F}$ gene.

```
Forward primer huCD38F-HindIII-2:
                                   (SEQ ID NO: 15)
TTGTAAGCTTGCCGCCACCATGGCTAACTGCGAGTTCTCC;

Reverse primer huCD38-S274F-R2-XhoI:
                                   (SEQ ID NO: 17)
TGGTCTCGAGTCAGATCTCGGAGGTGCAGCTGGAGTCTTCGGGGTTCTTC

ACGCACTGTAAAAACTTATCGGGCCTATAGATATT
```

The hCD38-$S_{274F}$ gene fragments were cloned into cell expression vector pQY-DHFR (self-made), then transferred into E. coli, and the positive recombinant plasmid pQY-DHFR-HCD38-$S_{274F}$ was identified through endonuclease digestion.

After that, the recombinant plasmid pQY-DHFR-HCD38-$S_{274F}$ was mixed with Fugen-6 liposome (Roche), then transfected into CHO-dhfr cells. After transfection and screening by IMDM culture medium containing FBS, the CHO cell lines stably expressing human CD38 gene with a point mutation (CHO/hCD38-$S_{274F}$) were obtained.

11.2 Detecting Binding of Murine Monoclonal Antibody m29, Human-Mouse Chimeric Antibody ch29G, and Daratumumab to CHO Cell Lines Expressing Wild-Type CD38 or CD38 with Point Mutation by Flow Cytometer In the present example, the binding of murine monoclonal antibody m29, human-mouse chimeric antibody ch29G, and Daratumumab to CHO cell lines expressing wild-type CD38 or CD38 with point mutation was detected by flow cytometer.

The main detecting steps were as follows: CHO cells stably expressing wild-type or point mutation of CD38 were respectively incubated with murine monoclonal antibody m29, human-mouse chimeric antibody ch29G, or Daratumumab at 4° C. for 1 hour, after washing with PBS-0.1% FCS solution, FTTC-Goat anti-Mouse IgG or FITC-Goat anti-Human IgG was added, incubated at 4° C. for 1 hour, then washing with PBS-0.1% FCS solution again, the samples were loaded into Accuri C6 Plus Flow Cytometer (BD, USA) for testing.

Figure 10A:
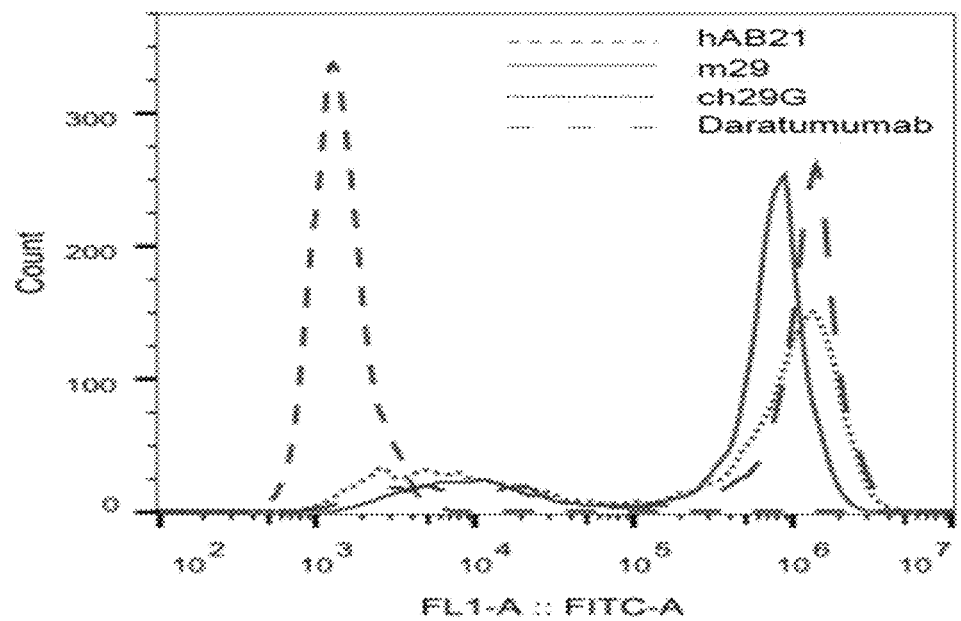
FIG. 10A is a detecting result diagram of CHO cell lines transfected and expressed with wild-type human CD38.
Figure 10B:
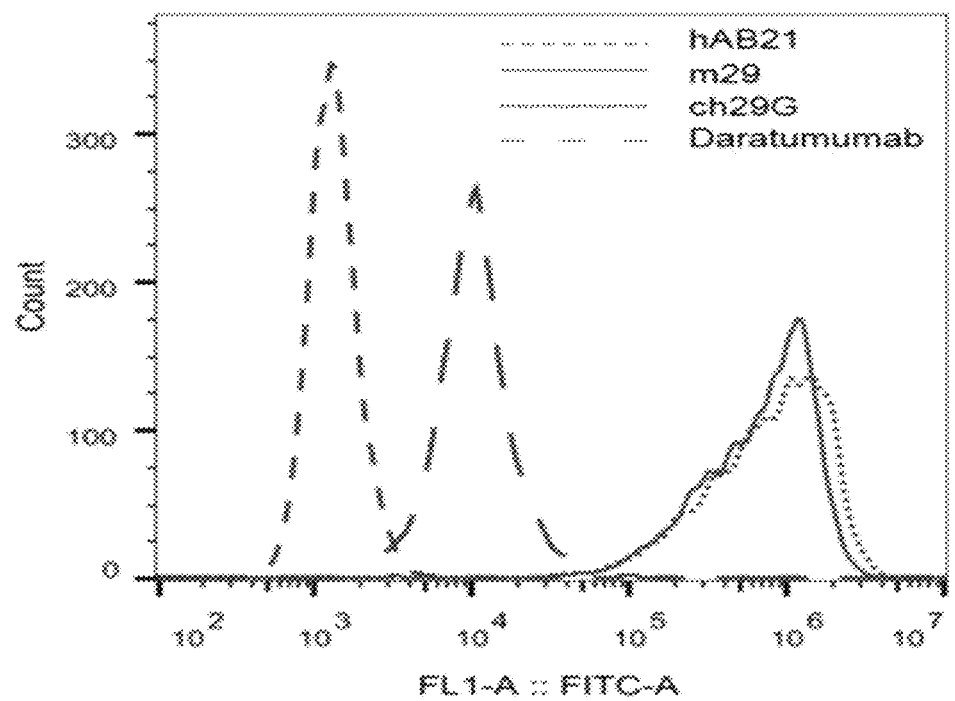
FIG. 10B is a detecting result diagram of CHO cell line stransfected and expressed with human CD38 with a point mutation (CHO/hCD38-$S_{274F}$)

FIGS. 10A-10B are the schematic diagrams of the representative results by flow cytometer, wherein FIG. 10A is a detecting result diagram of CHO cell lines expressing wild-type human CD38; it showed that the same with murine monoclonal antibody m29, human-mouse chimeric antibody ch29G retained the binding to CHO cell lines expressing wild-type human CD38 (CHO/hCD38-wild-type) and the binding strength of both of them is similar to that of Daratumumab.

FIG. 10B is a detecting result diagram of CHO cells expressing CD38 with a point mutation (CHO/hCD38-$S_{274F}$); it showed that the same with murine monoclonal antibody m29, human-mouse chimeric antibody ch29G also retained the binding to CHO cells expressing CD38 with a point mutation (CHO/hCD38-wild-type); in contrast, Daratumumab did not bind to CHO cells expressing CD38 with point mutation.

Example 12: Construction of CHO Cell Lines (CHO/mkCD38) Stably Expressing Synomolgus Macaque CD38 and Detecting Binding of Murine Monoclonal Antibody m29, Human-Mouse Chimeric Antibody ch29G, and Daratumumab to them 12.1 Construction of CHO Cell Lines (CHO/mkCD38) Stably Expressing Cynomolgus Macaque CD38

The amino acid sequences comparison analysis of human CD38 protein, cynomolgus macaque (Cynomolgus monkey) CD38 protein, and chimpanzee (Pan troglodytes) CD38 protein was shown in FIG. 11A. As shown in FIG. 11A, the amino acid sequence of chimpanzee CD38 protein (ChiCD38) was almost the same with human CD38 protein (huCD38); instead, the amino acid sequence of cynomolgus macaque CD38(mkCD38) protein was of 91% identity to that of human CD38 protein, but there were 16 differences between two amino acid sequences.

According to the gene sequence of cynomolgus macaque CD38 published in Genbank (Gene ID: 102126394), the responding cDNA fragments coding cynomolgus macaque CD38 were delegated to Suzhou Genewiz Biological Technology Co. LTD to synthesize, then cloned into the expression plasmid pQY-DHFR (self-made), transferred into *E. coli*, later the positive recombinant plasmid pQY-DHFR-mkCD38 was identified through endonuclease digestion.

After that, the recombinant plasmid pQY-DHFR-mkCD38 was mixed with Fugen-6 liposome (Roche), then co-transfected into DHFR gene deficiency CHO cells (CHO-dhfr). After transfection, screened by IMDM culture medium containing FBS, the cell lines expressing cynomolgus macaque CD38 protein (CHO-cynomolgus CD38) were obtained.

12.2 Detecting Binding of Murine Monoclonal Antibody m29, Human-Mouse Chimeric Antibody ch29G, and Daratumumab to CHO Cell Lines Stably Expressing Cynomolgus Macaque CD38 (CHO-Cynomolgus CD38) by Flow Cytometer The binding of murine monoclonal antibody m29, human-mouse chimeric antibody ch29G, and Daratumumab to CHO cell lines stably expressing cynomolgus macaque CD38 (CHO-cynomolgus CD38) was detected by the flow cytometer method described in section 11.2 of Example 11.

Figure 11B:
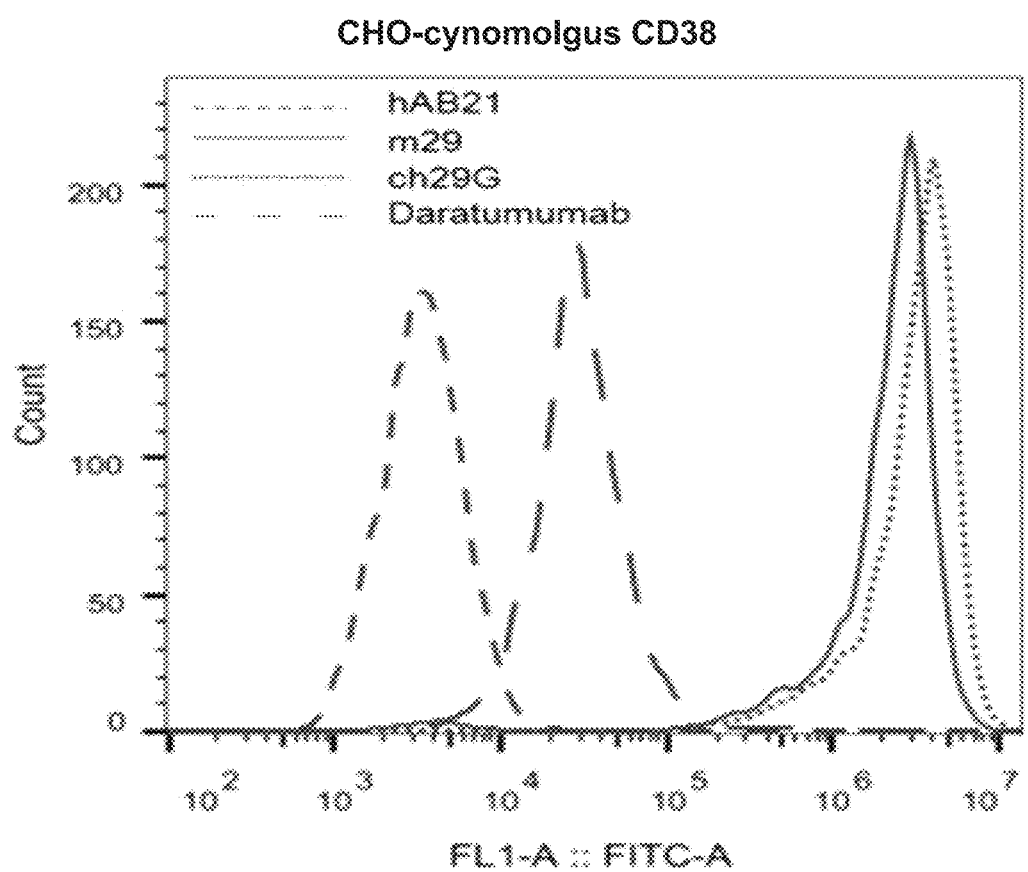
FIG. 11B is a binding result diagram of determining the binding of the mouse monoclonal antibody m29 sample, the human-mouse chimeric antibody ch29G, and the control sample Daratumumab to CHO cells stably transfected and expressed with cynomolgus macaque CD38 (CHO-cynomolgus CD38) in Example 12 of the present invention; wherein the negative control sample is the non-related humanized monoclonal antibody hAB21 (anti-human PD-1 monoclonal antibody).

FIG. 11B is a schematic diagram of the representative results by flow cytometer, and the result showed that the human-mouse chimeric antibody ch29G and the mouse monoclonal antibody m29 retained the same high affinity to CHO cells (CHO-cynomolgus CD38) stably expressing cynomolgus macaque CD38; instead, the binding intensity of Daratumumab to CHO cells expressing cynomolgus macaque CD38 was reduced by more than 90%.

Figure 12A:
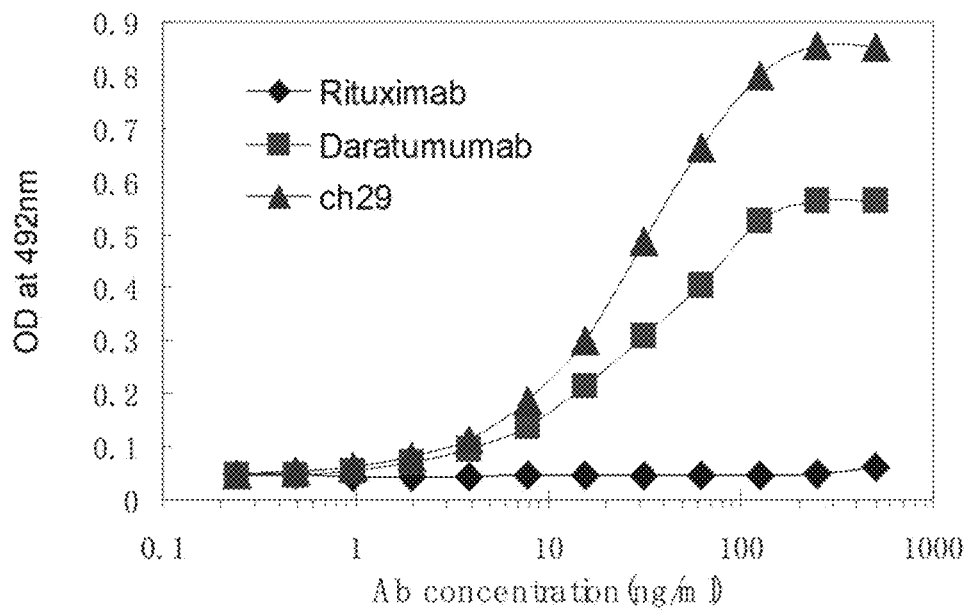
FIGS. 12A-12B are the binding result diagrams of detecting and comparing the binding of the human-mouse chimeric antibody ch29G sample and Daratumumab to recombinant human CD38 protein (FIG. 12A) and recombinant cynomolgus macaque CD38 protein (FIG. 12B) in Example 13 of the present invention; wherein the negative control sample is Rituximab (brand name: Rituxan, the human-mouse chimeric anti-CD20 monoclonal antibody).
Figure 12B:
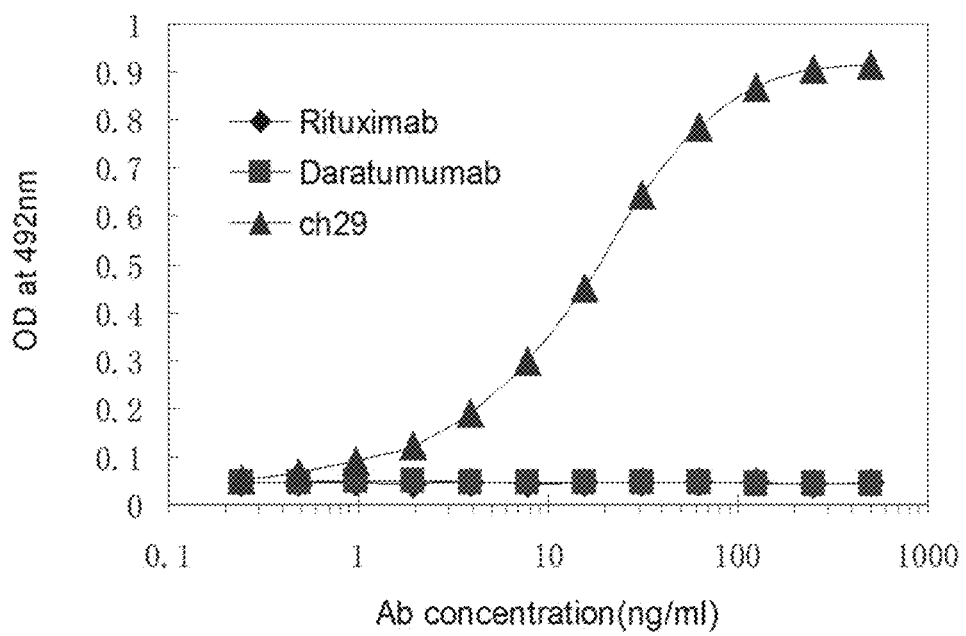

Example 13: Detecting Binding of Human-Mouse Chimeric Antibody ch29G and Daratumumab to Human CD38 Protein or Cynomolgus Macaque CD38 Protein by ELISA In the present example, the binding of the human-mouse chimeric antibody ch29G and Daratumumab to the recombinant human CD38 protein or the recombinant cynomolgus macaque CD38 protein was detected by direct ELISA. For this purpose, the 96-well cell culture plates were coated with the recombinant human CD38-his protein (Sino Biological Inc.) or the recombinant cynomolgus macaque CD38-his protein (Sino Biological Inc.) (1 μg/ml, 50 μl/well, 4° C. overnight), sealed with 5% milk; After that, the human-mouse chimeric antibody ch29G sample, Daratumumab, and negative control antibody Rituximab (anti-human CD20 monoclonal antibody) were diluted to 1 ug/ml with diluent (PBST-5% milk), then loaded to 96-well plates coated with CD38 protein, 12 wells were diluted in 2-fold serial dilution, incubated at room temperature for 1 hour; after thoroughly washing with PBS-0.1% Tween20 solution, HRP enzyme labeled Goat-anti-human-IgG was added as a testing second antibody (diluted at 1:1000, purchased from Shanghai Xitang Biology company), incubated at room temperature for 1 hour; after thoroughly washing with PBS-0.1% Tween20 solution again, the substrate solution OPD-0.1% $H_2O_2$ was added for staining about 10-15 minutes at room temperature, then 1M HCl solution was added to quench the reaction, then the OD values at 492 nm wavelength were read in a multimode reader (PerkinElmer Victor X3) FIG. 12 is the detecting results by ELISA. As shown in FIGS. 12A-12B, the human-mouse chimeric antibody ch29G and Daratumumab retained the same high affinity to human CD38 protein (FIG. 12A). The human-mouse chimeric antibody ch29G also retained a high affinity to cynomolgus macaque CD38 protein; In contrast, Daratumumab can not significantly bind to cynomolgus macaque CD38 protein (FIG. 12B).

Example 14: Comparing and Analyzing Activities of Human-Mouse Chimeric Antibody ch29G and Daratumumab by CDC Method In Vitro 14.1 Materials and Method In the present example, CDC activities of the human-mouse chimeric antibody ch29G to several target cells (including Daudi, Raji, MOLT-4, and Jurkat, etc.) were detected by CDC method described in Example 2, and the results were compared with that of Daratumumab. Wherein the complement used came from the serum of healthy people (10%, self-made), the CDC positive control sample was Rituximab (anti-CD20 human-mouse chimeric monoclonal antibody), and the negative control sample was hPV19 monoclonal antibody (a humanized anti-VEGF monoclonal antibody).

FIGS. 13A-13D were the CDC activities results, wherein

Figure 13A:
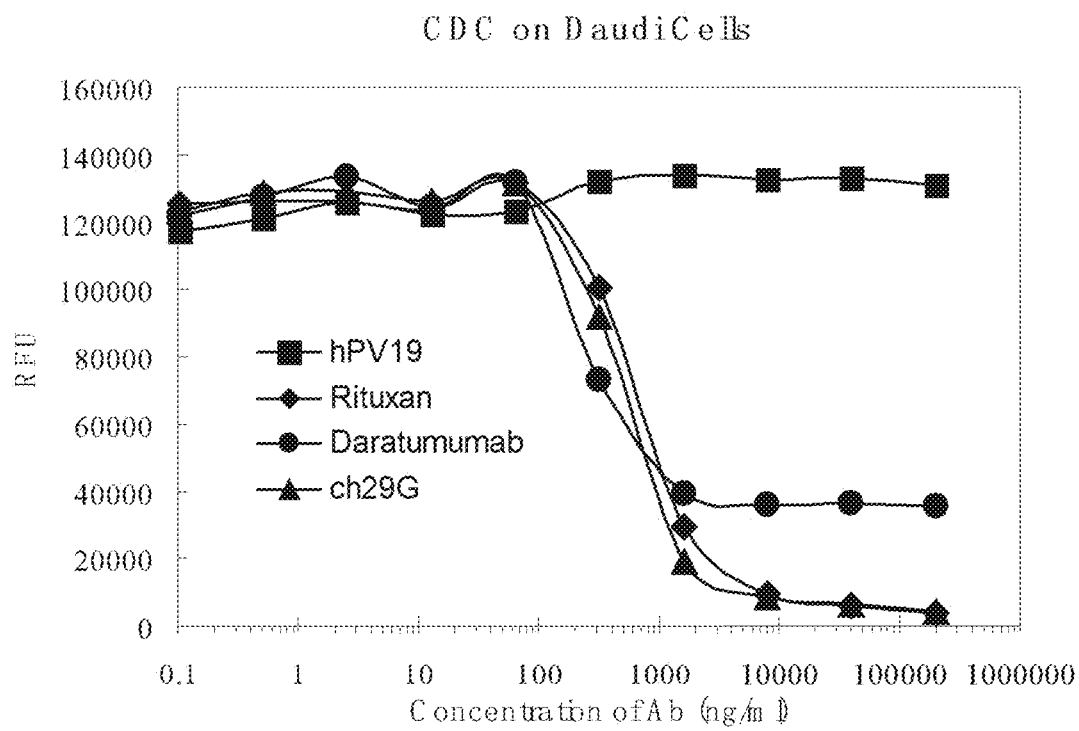

FIG. 13A was the CDC activities testing results targeting Daudi, and the results showed that the human-mouse chimeric antibody ch29G had similar CDC activity to the positive control sample Rituximab; in addition, the CDC activities of both were stronger than Daratumumab.

Figure 13B:
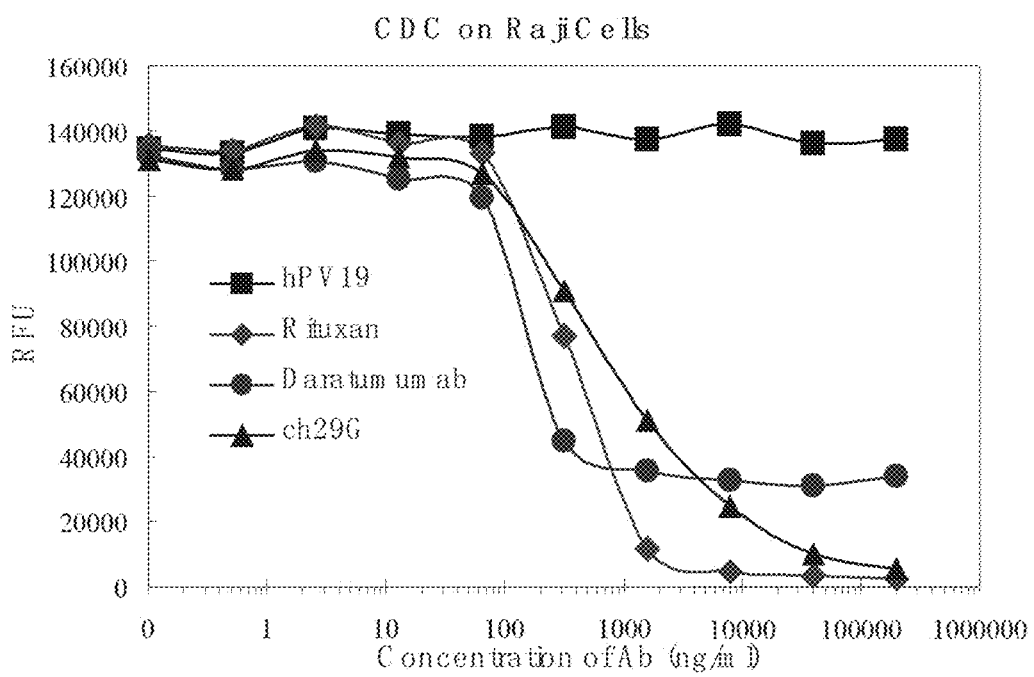

FIG. 13B was the CDC activities testing results targeting Raji, and the results showed that the human-mouse chimeric antibody ch29G also had similar CDC activity to the positive control sample Rituximab; in addition, the CDC activity of Daratumumab was also similar to human-mouse chimeric antibody ch29G.

Figure 13C:
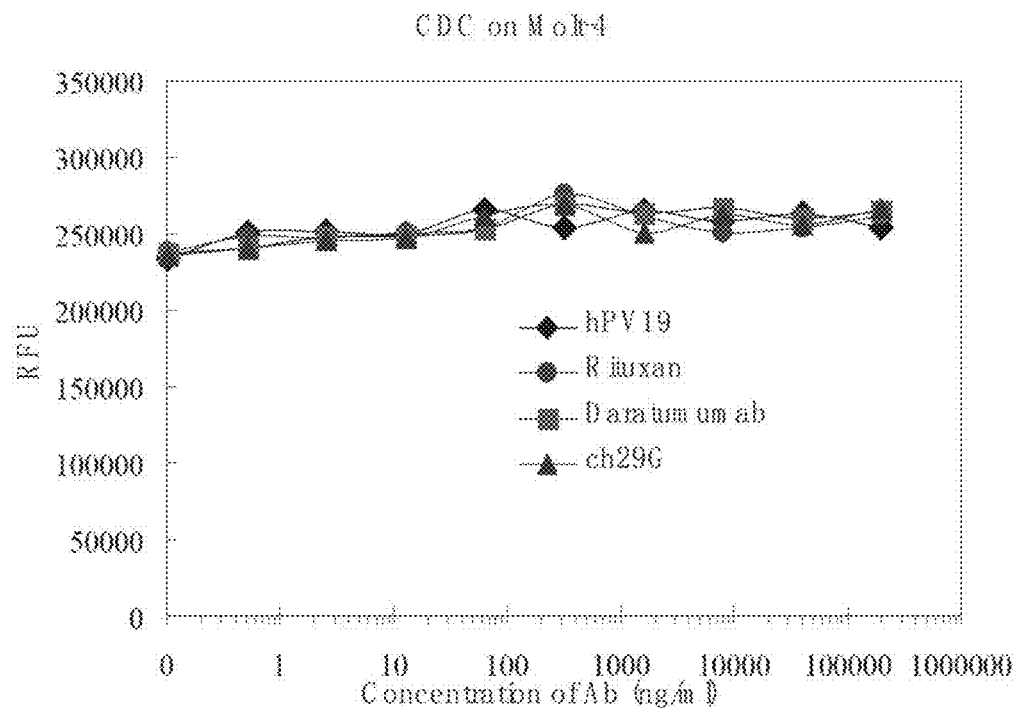

FIG. 13C was the CDC activities testing results targeting MOLT-4, and the results showed that the human-mouse chimeric antibody ch29G, Daratumumab, and Rituximab had no significant CDC activities.

Figure 13D:
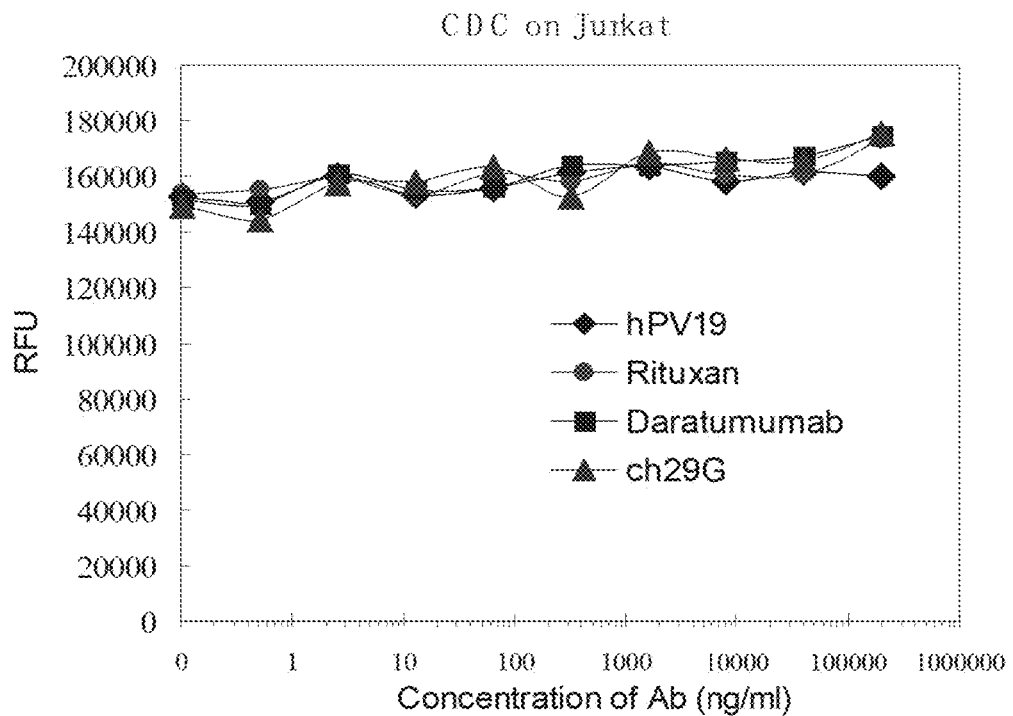

FIG. 13D was the CDC activities testing results targeting Jurkat, and the results showed that the human-mouse chimeric antibody ch29G, Daratumumab, and Rituximab also had no significant CDC activities.

Example 15: Humanization Genetic Engineering of Murie Antibody m29

After ELISA and CDC testing, etc., human-mouse chimeric antibody ch29G's high affinity and CDC activity to human CD38 were preliminary proved, on this basis, a series of genetic engineering cloning methods such as PCR were used to transplant the antigen complementarity-determining regions (CDRs) gene fragments in the chimeric antibody light chain to the corresponding human Kappa light chain variable framework regions (FR), the light chain of humanized antibody was obtained; then the light chain was combined with a chimeric heavy chain, accordingly, the light chain humanized HH29G antibody was achieved.

15.1 Humanization Genetic Engineering of Murine m29 Antibody Light Chain

Through amino acid sequences analysis, the expression product of the first V germline Gene of human immunoglobulin Kappa light chain (IgKV2D-29, NCBI Gene ID: 28882) was determined to have the highest identity with the light chain variable region of murine m29 antibody. Accordingly, the light chain framework region (FR) of m29 antibody was replaced with the homologous sequence of human IGKV2D-29, then the replaced variable region gene was spliced with the sequence coding the light chain constant region of human immunoglobulin IgG-Kappa, and finally, the humanized light chain coding gene (H29-L) was successfully obtained. The amino acid sequence of the light chain variable region of the humanized m29 antibody was shown in SEQ ID NO:11, and its nucleotide sequence was shown in SEQ ID NO: 13.

15.2 Humanization Genetic Engineering of Murine m29 Antibody Heavy Chain

Through amino acid sequences analysis, the expression product of the first V germline Gene of human immunoglobulin Kappa heavy chain (IGHV1-69, NCBI Gene ID:28461) was determined to have the highest identity with the heavy chain variable region of m29. Accordingly, the heavy chain framework region (FR) of m29 was replaced with the homologous sequence of human IGHV1-69, then the replaced variable region gene was spliced with the coding sequence of the heavy chain constant region of human immunoglobulin IgG, and finally, the humanized heavy chain coding gene (h29-h) was successfully obtained. The amino acid sequence of the heavy chain variable region of the humanized m29 antibody was shown in SEQ ID NO: 12, and its nucleotide sequence was shown in SEQ ID NO: 14.

Example 16: Construction of CHO Engineering Cell Lines Stably and High Efficacy Expressing Humanized or Half Humanized HH29 Monoclonal Antibody(HH29) and Isolation and Purification of Antibody Protein The human-mouse chimeric heavy chain gene (ch29H) and the humanized light chain gene (HH29L) were cloned step-by-step to the expression vector pQY-Dhfr-Hex, then transferred into L: co/i, amplified and isolated to obtain the expression plasmid containing humanized or half humanized HH29 monoclonal antibody (HH-29). The recombinant plasmid expressing the light chain humanized antibody HH29 was transiently transfected into CHO cells. 24 hours after transfection, the cell supernatant was sucked from the wells, and CD38-his protein was used as the coated antigen, HRP-Goat anti-Human IgG was used as a secondary antibody (purchased from Shanghai Xitang Biological Company), OPD was used as the chromogenic substrate, then the binding activity of antibody in the transfected cell supernatant to the human CD38 protein antigen was detected by direct ELISA.

Table 4 was the representative results of the ELISA.

TABLE 4

Analyzing the binding activity of transiently transfected cell culture supernatant to human CD38 protein

| Supernatant Dilution Times | OD Values | |
|---|---|---|
| | ch29 | HH29 |
| 2 | 0.989 | 1.177 |
| 4 | 0.945 | 1.163 |
| 8 | 0.789 | 1.105 |
| 16 | 0.603 | 0.811 |
| 32 | 0.431 | 0.508 |
| 64 | 0.313 | 0.325 |
| 128 | 0.212 | 0.178 |
| 256 | 0.121 | 0.110 |

As shown in Table 4, like human-mouse chimeric monoclonal antibody ch29G, half humanized monoclonal antibody HH29 (light chain humanized) retained the binding activity to human CD38 protein.

The above-transfected cells were adapted by clonal screening and serum-free medium suspension culture, several CHO engineering cell lines with a stable and efficient expression of half humanized monoclonal antibody HH29 (light chain humanized) were obtained.

Later, one engineering cell line was chosen to amplify in a serum-free medium, and the culture supernatant was collected. After centrifugation and filtration with a 0.45 μm filtration membrane, HH29 antibody with high purity (protein purity >99%) was obtained after multiple purification steps including a Protein-A affinity chromatography column (protein A-Sepharose Fast Flow, GE, USA, ion exchange column separation, virus removal/inactivation, and filtration/sterilization (0.22 μm filtration membrane). The purified HH29 monoclonal antibody was dissolved in glycine-Tris buffer (pH=7.0) (1-10 mg/mL) and stored at low temperature (about 4° C.).

Example 17: Detecting Anti-Tumor Efficacy of Mouse Monoclonal Antibody m29 In Vivo In the present example, the anti-tumor efficacy of murine monoclonal antibody m29 was tested in vivo by subcutaneous inoculation of human B-lymphoma Raji tumor model in nude mice, and the human-mouse chimeric anti-CD20 monoclonal antibody Rituximab was used as a positive control drug. Human B-lymphoma cell lines Raji were first inoculated subcutaneously in nude mice; after the tumor was formed in test animals, the animals were divided into groups and administered, and the tumor growth was observed and recorded.

Therefore, $1 \times 10^7$ human B-lymphoma cell line Raji cells (Typical Culture Preservation Commission Cell Bank, Chinese Academy of Sciences) were inoculated in nude mice (purchased from Nanjing University Animal Center). when tumor volume inoculated grew to about soybean volume (about 100 mm$^3$, approximately 6-7 days after tumor cells were inoculated), the animals were randomly divided into the following three groups:

Group A: normal saline negative control group (n=2, equal volume normal saline)

Group B: positive control drug Rituximab treatment group (n=4, the dose was 10 mg/kg body weight)

Group C: m29 monoclonal antibody treatment group (n=4, the dose was 10 mg/kg body weight)

From the same day (i.e., 6-7 days after tumor inoculation), the animals were administered intraperitoneal injection (i.p.), twice a week (every 3-4 days) and six times consecutively (3 weeks). During the administering period, the general clinical symptoms of the animals were observed every day, and the tumor long diameter (mm) and short diameter (mm) and animal weight were measured every 3-4 days. The tumor volume calculation formula is volume (mm$^3$)=long diameter (mm)×short diameter (mm)×short diameter (mm)× 0.5. If the tumor volume exceeded 3,000 mm$^3$ at the time of measurement, the tested animals would be euthanized.

Figure 14A:
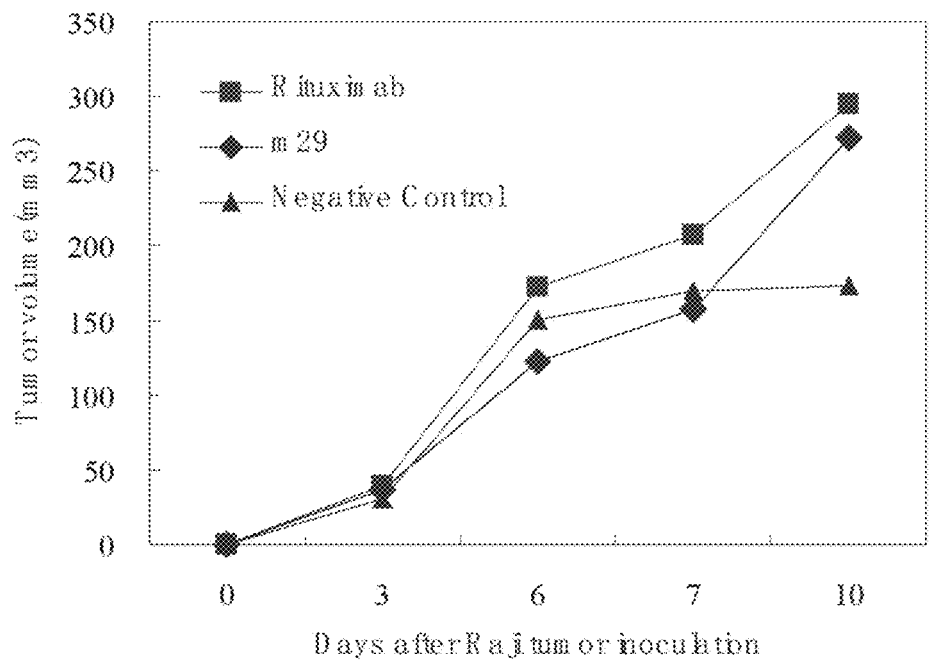
Figure 14B:
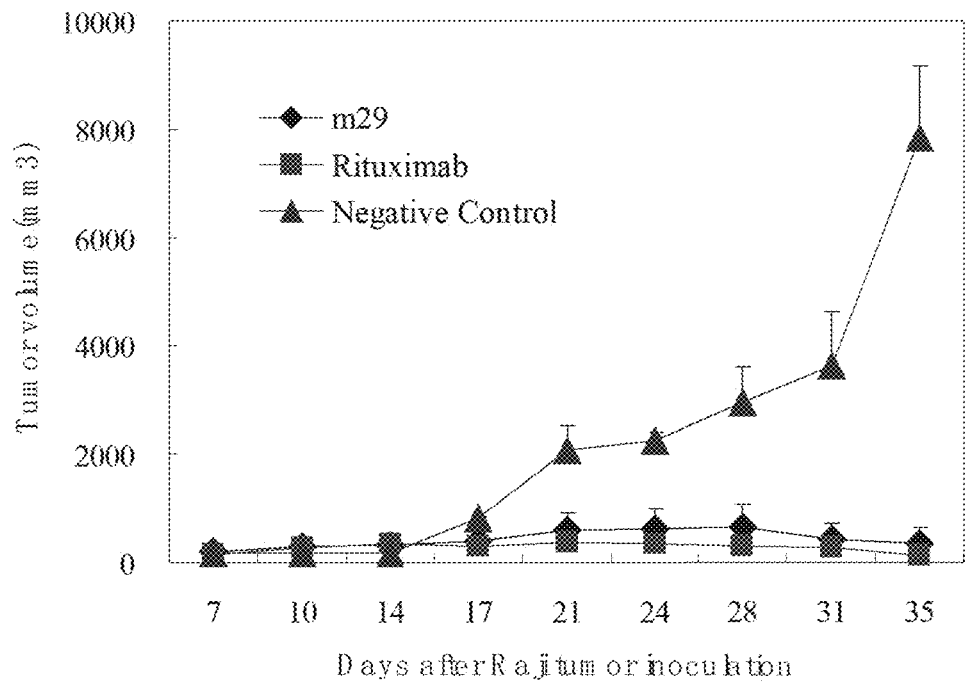

Test Results:

FIGS. 14A-14B showed the average tumor growth volume trend of animals in each experimental group FIG. 14A is a schematic diagram of average tumor growth volume ten days before inoculation, and the results showed that no significant difference between the groups.

FIG. 14B is a schematic diagram of the average growth volume of the tumor at the later stage of inoculation. The results showed that, compared with the normal saline negative control group, the tumors in m29 monoclonal antibody treatment group and the positive control drug Rituximab treatment group were significantly reduced or even completely disappeared.

Example 18: Testing Anti-Tumor Efficacy of Human-Mouse Chimeric Antibody ch29G In Vivo In the present example, the anti-tumor efficacy of the human-mouse chimeric antibody ch29G was tested in vivo by subcutaneous inoculation of human B-lymphoma Raji tumor model in nude mice by the same method described in Example 17, and Daratumumab was used as a positive control drug. Human B-lymphoma cell lines Raji were first inoculated subcutaneously in nude mice. After the tumor was formed in test animals, the animals were divided into groups and administered, and the tumor growth was observed and recorded.

Therefore, 1×10$^7$ human B-lymphoma cell line Raji cells were inoculated in nude mice (Purchased from Nanjing University Animal Center), when the tumor volume inoculated grew to about soybean volume (about 100 mm$^3$, approximately 6-7 days after tumor cells were inoculated), the animals were randomly divided into the following three groups:

Group A: normal saline negative control group (n=2, equal volume normal saline)

Group B: positive control drug Daratumumab group (n=10, the dose was 5 mg/kg body weight)

Group C: ch29G monoclonal antibody treatment group (n=10, the dose was 2.5 mg/kg body weight)

From the same day (i.e., 6-7 days after tumor inoculation), the animals were administered intraperitoneal injection (i.p.), twice a week (every 3-4 days) and six times consecutively (3 weeks). During the administering period, the general clinical symptoms of the animals were observed every day, and the tumor long diameter (mm), short diameter (mm), and animal weight were measured every 3-4 days. The tumor volume calculation formula is volume (mm) =long diameter (mm)×short diameter (mm)×short diameter (mm)×0.5. If the tumor volume exceeded 3,000 mm$^3$ at the time of measurement, the tested animals would be euthanized.

Figure 15:
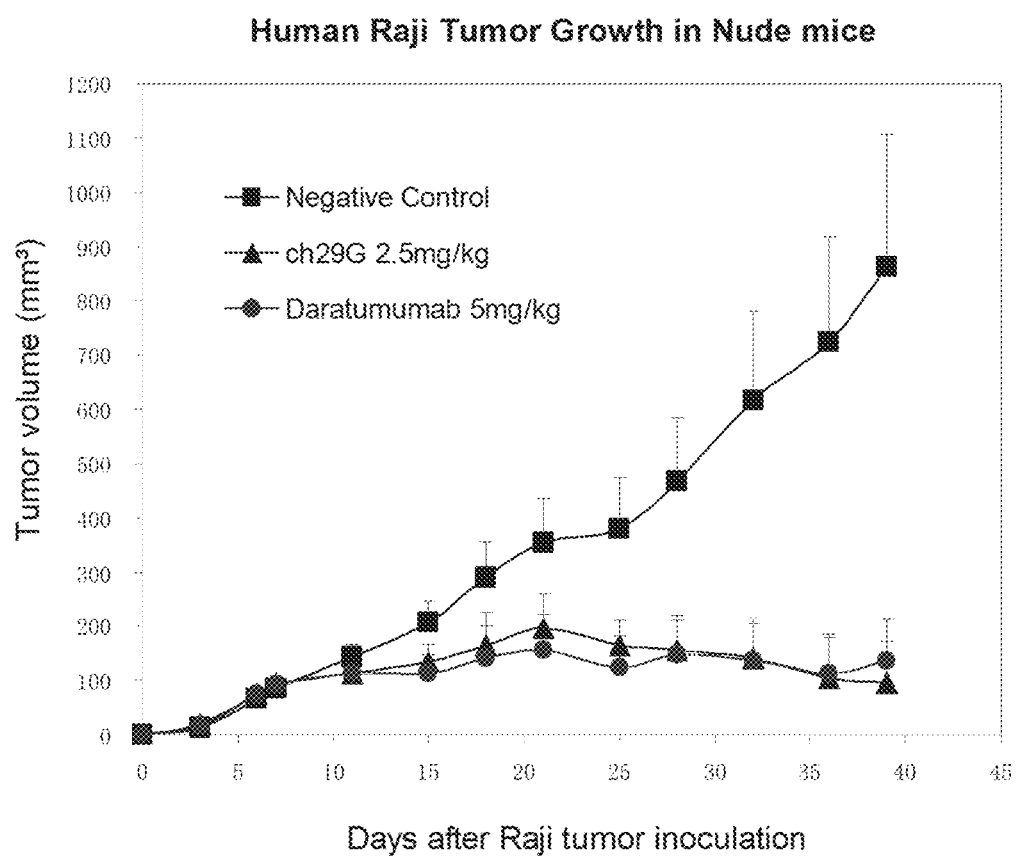
FIG. 15 is an anti-tumor efficacy result diagram in vivo of detecting the human-mouse chimeric antibody ch29G in Raji tumor model inoculating human B-lymphoma cells subcutaneously in nude mouse in Example 18 of the present invention.

Test Results:

FIG. 15 showed the average tumor growth volume trend of animals in each experimental group, and the results showed that, compared with the normal saline negative control group, the growth of the tumors in ch29G monoclonal antibody treatment group and the positive control drug Daratumumab treatment group were significantly inhibited, the therapeutic efficacy of ch29G monoclonal antibody in a dose of 2.5 mg/kg body weight was similar to Daratumumab in a dose of 5 mg/kg body weight.

REFERENCES

1. Jackson D G and Bell J I. Isolation of a cDNA encoding the human CD38 (T10) molecule, a cell surface glycoprotein with an unusual discontinuous pattern of expression during lymphocyte differentiation. *J. Immunol.* 1990, 144:2811-2815.
2. Harada N, Santos-Argumedo L, Chang R, Grimaldi J C, Lund F E, Brannan C I, Copeland N G, Jenkins N A, Heath A W, Parkhouse R M, et al. Expression cloning of a cDNA encoding a novel murine B cell activation marker. homology to human CD38. *J Immunol.* 1993, 151:3111-8.
3. Ferrero E, Orciani M, Vacca P, Ortolan E, Crovella S, Titti F, Saccucci F, Malavasi F. Characterization and phylogenetic epitope mapping of CD38 ADPR cyclase in the cynomolgus macaque. *BMC Immunol.* 2004, 5:21.
4. States D J, Walseth T F and Lee H C. Similarities in amino acid sequences of Aplysia ADP-ribosyl cyclase and human lymphocyte antigen CD38. *Trends Biochem. Sci.* 1992, 17:495.
5. Howard M, Grimaldi J C, Bazan J F, Lund F E, Santos-Argumedo L, Parkhouse R M, Walseth T F, Lee H C: Formation and hydrolysis of cyclic ADP-ribose catalyzed by lymphocyte antigen CD38. *Science.* 1993, 262:105.
6. Summerhill R J, Jackson D G, Galione A. Human lymphocyte antigen CD38 catalyzes the production of cyclic ADP-ribose. *FEBS Lett.* 1993, 335:231-233.
7. Sridhar Prasad, Duncan E. McRee, Enrico A. Stura, David G. Levitt, Hon Cheung Lee & C. David Stout.
Crystal structure of Aplysia ADP ribosyl cyclase, a homologue of the bifunctional ectoenzyme CD38. *Nature Structural Biology* 1996, 3: 957-964.
8. Mehta K, Shahid U and Malavasi F (Review): Human CD38, a cell-surface protein with multiple function. *FASEB J.* 1996, 10; 1408-1417.
9 George Shubinsky, Michael Schlesinger(Review): The CD38 Lymphocyte Differentiation Marker: New Insight into Its Ectoenzymatic Activity and Its Role as a Signal Transducer. *Immunity* 1997, 7:315-324.
10. Stevenson F K, Bell A J, Cusack R, Hamblin T J, Slade C J, Spellerberg M B, Stevenson G T.
Preliminary studies for an immunotherapeutic approach to the treatment of human myeloma using chimeric anti-CD38 antibody. *Blood.* 1991, 77:1071-1079.
11. Goldmacher V S, Bourret L A, Levine B A, Rasmussen R A, Pourshadi M, Lambert J M, Anderson K C.
Anti-CD38-blocked ricin: an immunotoxin for the treatment of multiple myeloma. *Blood.* 1994, 84:3017-25.
12. Ellis J H, Barber K A, Tutt A, Hale C, Lewis A P, Glennie M J, Stevenson G T, Crowe J S. Engineered anti-CD38 monoclonal antibodies for immunotherapy of multiple myeloma. *J Immunol.* 1995, 155:925-937.
13. de Weers M, Tai Y T, van d V, Bakker J M, Vink T, Jacobs D C, et al. Daratumumab, a novel therapeutic human CD38 monoclonal antibody, induces killing of multiple myeloma and other hematological tumors. *J Immunol.* 2011, 186:1840-1848.
14. Lokhorst H M, Plesner T, Laubach J P, Nahi H, Gimsing P, Hansson M, et al. Targeting CD38 with Daratumumab Monotherapy in Multiple Myeloma. *N Engl J Med.* 2015, 373:1207-1219.

15. Lonial S, Weiss B M, Usmani S Z, Singhal S, Chari A, Bahlis N J, et al. Daratumumab monotherapy in patients with treatment-refractory multiple myeloma (SIRIUS): an open-label, randomised, phase 2 trial. *Lancet.* 2016, 387: 1551-1560.
16. Nijhof I S, Groen R W, Noort W A, van K B, de Jong-Korlaar R, Bakker J, et al. Preclinical evidence for the therapeutic potential of CD38-targeted immuno-chemotherapy in multiple myeloma matients refractory to lenalidomide and bortezomib. *Clin Cancer Res.* 2015, 21:2802-10.
17. Plesner T, Arkenau H T, Gimsing P, Krejcik Lemech C, Minnema M C, et al. Phase 1/2 study of daratumumab, lenalidomide, and dexamethasone for relapsed multiple myeloma. *Blood.* 2016, 128:1821-28.
18. Palumbo A, Chanan-Khan A, Weisel K, Nooka A K, Masszi T, Beksac M, et al (CASTOR Investigators) Daratumumab, bortezomib, and dexamethasone for multiple myeloma. *N Engl J Med.* 2016, 375:754-66.
19. Dimopoulos M A, Oriol A, Nahi H, San-Miguel J, Bahlis N J, Usmani S Z, et al (POLLUX Investigators). Daratumumab, lenalidomide, and dexamethasone for multiple myeloma. *N Engl J Med.* 2016, 375:1319-1331.
20. Ajai Chari, et al. (EQUULEUS; MMY1001 Investigators): Daratumumab plus pomalidomide and dexamethasone in relapsed and/or refractory multiple myeloma. *Blood.* 2017, 130: 974-981.
21. Mateos M-V et al (ALCYONE Trail Investigators). Daratumumab pls bortezomib, melphalan and prednisone for untreated myeloma. *N Engl J Med.* 2018, 378:518-528.

We claim:

1. A monoclonal antibody or a derivative thereof, wherein the monoclonal antibody or the derivative thereof specifically binds human and monkey CD38 antigens, and comprises a first variable region and a second variable region,
wherein the first variable region is an antibody light chain variable region comprising complementarity-determining regions CDR1, CDR2, and CDR3 having the amino acid sequences as set forth in SEQ ID NO: 3, SEQ ID NO: 4 and SEQ ID NO: 5, respectively; and
wherein the second variable region is an antibody heavy chain variable region comprising complementarity-determining regions CDR1, CDR2, and CDR3 having the amino acid sequences as set forth in SEQ ID NO: 8, SEQ ID NO: 9 and SEQ ID NO: 10, respectively.

2. The monoclonal antibody or the derivative thereof according to claim 1, wherein the first variable region is an antibody light chain variable region having the amino acid sequence as set forth in SEQ ID NO: 2; and the second variable region is an antibody heavy chain variable region having the amino acid sequence as set forth in SEQ ID NO: 7.

3. The monoclonal antibody or the derivative thereof according to claim 1, wherein the first variable region is an antibody light chain variable region having the amino acid sequence as set forth in SEQ ID NO: 11; and wherein the second variable region is an antibody heavy chain variable region having the amino acid sequence as set forth in SEQ ID NO: 12 or SEQ ID NO: 7.

4. The monoclonal antibody or the derivative thereof according to claim 1, comprising the antibody tight chain variable region, a human antibody light chain constant region, the antibody heavy chain variable region, and a hinge region of a human antibody heavy chain constant region, CH1 region, CH2 region, and 013 region.

5. The monoclonal antibody or the derivative thereof according to claim 4, wherein the human antibody light chain constant region is a kappa chain or a lambda chain of a human antibody, the human antibody heavy chain constant region is one selected from the group consisting of human IgG 1, IgG2, IgG3, and IgG4 isotype.

6. A DNA molecule or gene coding the monoclonal antibody or the derivative thereof according to claim 3, wherein the nucleotide sequence of the antibody light chain variable region is as set forth in SEQ ID NO: 1 or SEQ ID NO: 13, and the nucleotide sequence of the antibody heavy chain variable region is as set forth in SEQ ID NO: 6 or SEQ ID NO: 14.

7. An expression vector comprising the DNA sequence of the DNA molecule of claim 6 and an expression regulatory sequence operably linked to the DNA sequence.

8. A recombinant host cell, wherein the recombinant host cell is transfected with the expression vector of claim 7.

9. The recombinant host cell according to claim 8 or a progeny cell thereof, wherein the recombinant host cell or the progeny cell thereof expresses the monoclonal antibody or the derivative thereof.

10. A pharmaceutical compound or a pharmaceutical composition, comprising the monoclonal antibody or the derivative thereof of claim 1, and a pharmaceutically accepted carrier.

11. A method of using the pharmaceutical compound or pharmaceutical
composition according to claim 10 as a medicament for the treatment of tumors, the method comprising treating a subject in need thereof with the pharmaceutical compound or pharmaceutical composition of claim 10.

12. The method according to claim 11, wherein the tumors are CD38-positive tumors.

13. The method according to claim 12, wherein the CD38-positive tumors are human myeloma or human lymphoma.

14. A method for preparing the monoclonal antibody or the derivative thereof
of claim 1, wherein the method comprises the following steps:
a) providing an expression vector, wherein the expression vector comprises a DNA molecular sequence that encodes the antibody or the derivative thereof of claim 1 and an expression regulatory sequence operably linked to the DNA molecular sequence;
b) transfecting a host cell with the expression vector of step a);
c) culturing the host cell from step b) under conditions suitable for an expression of the monoclonal antibody or the derivative thereof; and
d) isolating, purifying, and collecting the monoclonal antibody or the derivative thereof from a host cell culture medium by an affinity chromatography.

15. The monoclonal antibody or the derivative thereof according to claim 2, comprising the antibody light chain variable region, a human antibody light chain constant region, the antibody heavy chain variable region, and a hinge region of a human antibody heavy chain constant region, CMI region, CH2 region, and CH3 region.

16. The monoclonal antibody or the derivative thereof according to claim 3, comprising the antibody light chain variable region, a human antibody light chain constant region, the antibody heavy chain variable region, and a hinge region of a human antibody heavy chain constant region, CH1 region, CH2 region, and CH3 region.

17. The recombinant host cell according to claim 8 or the progeny cell thereof, wherein the monoclonal antibody or the derivative thereof comprises the antibody light chain variable region, a human antibody light chain constant region, the antibody heavy chain variable region, and a hinge region of a human antibody heavy chain constant region, CHI region, CH2 region, and CH3 region,
 wherein the human antibody light chain constant region is a kappa chain or a lambda chain of a human antibody, the human antibody heavy chain constant region is one selected from the group consisting of human IgG 1, IgG2, IgG3, and IgG4 isotypes.

18. The pharmaceutical compound or the pharmaceutical composition according to claim 10, wherein the monoclonal antibody or the derivative thereof comprises the antibody light chain variable region, a human antibody light chain constant region, the antibody heavy chain variable region, and a hinge region of a human antibody heavy chain constant region, CH1 region, CH2 region, and CH3 region,
 wherein the human antibody light chain constant region is a kappa chain or a lambda chain of a human antibody, the human antibody heavy chain constant region is one selected from the group consisting of human IgG 1, IgG2, IgG3, and IgG4 isotypes.

19. The method according to claim 14, wherein the antibody or the derivative thereof comprises the monoclonal antibody light chain variable region, a human antibody light chain constant region, the antibody heavy chain variable region, and a hinge region of a human antibody heavy chain constant region, CHI region, CH2 region, and CH3 region,
 wherein the human antibody light chain constant region is a kappa chain or a lambda chain of a human antibody, the human antibody heavy chain constant region is one selected from the group consisting of human IgG 1, IgG2, IgG3, and IgG4 isotypes.

\* \* \* \* \*